United States Patent [19]

Miller et al.

[11] Patent Number: 5,807,678
[45] Date of Patent: Sep. 15, 1998

[54] IDENTIFICATION OF GENE MUTATIONS ASSOCIATED WITH CONGENITAL LIPOID ADRENAL HYPERPLASIA

[75] Inventors: Walter L. Miller; Dong Lin, both of San Francisco, Calif.; Jerome F. Strauss, III, Wyndmoor, Pa.

[73] Assignee: Regents of the University of California, Oakland, Calif.

[21] Appl. No.: 410,540

[22] Filed: Mar. 23, 1995

[51] Int. Cl.[6] .............................. C12Q 1/68; C07H 21/02; C07H 21/04
[52] U.S. Cl. .............................. 435/6; 536/23.1; 536/24.3
[58] Field of Search ................................ 435/6; 536/22.1, 536/23.1, 24.3

[56] References Cited

PUBLICATIONS

J.F. Crivello et al., (1980) "Intracellular Movement of Cholesterol in Rat Adrenal Cells" *J. Biol. Chem*, 255:8144–8151.

C.R. Jefcoate et al., (1987) "ACTH Regulation of Cholesterol Movement in Isolated Adrenal Cells" *J. Steroid Biochem.* 27:721–729.

H.J. Degenhart et al., (1972) "Evidence for Deficient 20α–Cholesterol–Hydroxlase Activity in Adrenal Tissue of a Patient with Lipoid Adrenal Hyperplasia" *Acta Endocrinol.* 71:512–518.

Koizumi et al., (1977) "Cholesterol Side–Chain Cleavage Enzyme Activity and Cytochrome P–450 Content in Adrenal Mitochondria of a Patient with Congenital Lipoid Adrenal Hyperplasia (Prader Disease)" *Clinica Chimica Acta* 77:301–306.

Hauffa et al., (1985) "Congenital Adrenal Hyperplasia due to Deficient Cholesterol Side–Chain Cleavage Activity (20, 22–Desmolase) in a Patient Treated for 18 Years" *Clin. Endocrinol.* 23:481–493.

Sakai et al., (1994) "No Mutation in Cytochrome P450 Side Chain Cleavage in a Patient with Congenital Lipoid Adrenal Hyperplasia" *J. Clin. Endocrinol. Metab.* 79:1198–1201.

Lin et al., (1991) "Normal Genes for the Cholesterol Side Chain Cleavage Enzyme, P450scc, in Congenital Lipoid Adrenal Hyperplasia" *J. Clin. Invest.* 88:1955–1962.

Lin et al., (1993) "The Human Peripheral Benzodiazepine Receptor Gene: Cloning and Characterization of Alternative Splicing in Normal Tissues and in a Patient with Congenital Lipoid Adrenal Hyperplasia" *Genomics* 18:643–650.

Epstein et al., (1991) "Regulation of Steroid Hormone Biosynthesis: Identification of Precursors of a Phosphoprotein Targeted to the Mitochondrion in Stimulated Rat Adrenal Cortex Cells" *J. Biol. Chem.* 266(29):19739–19745.

Saenger et al., (1995) "Prenatal Diagnosis of Congenital Lipoid Adrenal Hyperplasia" *Journal of Clinical Endocrinology and Metabolism* 80(1):200–205.

Saenger et al., (1993) "Congenital Lipoid Adrenal Hyperplasia—Genes for P450scc, Side Chain Cleavage Enzyme, Are Normal" *J. Steroid Biochem. Molec. Biol.* 45:87–97.

Matteson et al., (1986) "Study of Cholesterol Side–CHain CLeavage (20,22 Desmolase) Deficiency Causing Congenital Lipoid Adrenal Hyperplasia Using Bovine–Sequence P450scc Oligodeoxyribonucleotide Probes" *Endocrinology* 118(4):1296–1305.

Clark et al., (1994) "The Purification, Cloning, and Expression of a Novel Luteinizing Hormone–induced Mitochondrial Protein in MA–10 Mouse Leydig Tumor Cells" *J. Biol. Chem.* 269(45):28314–28322.

Stocco et al., (1993) "The Use of Genetic Manipulation of MA–10 Leydig Tumor Cells to Demonstrate the Role of Mitochondrial Proteins in the Acute Regulation of Steroidogenesis" *Endocrinology* 132(3):959–967.

Fukami et al., (1995) "Lack of Mutations in P450scc Gene (CYP11A) in Six Japanese Patients with Congenital Lipoid Adrenal Hyperplasia" *Clin. Pediatr. Endocrinol.* 4(1):39–46.

Privalle et al., (1983) "Regulation of Intramitochondrial Cholesterol Transfer to Side–Chain Cleavage Cytochrome P–450 in Rat Adrenal Gland" *Proc. Natl. Acad. Sci. USA* 80:702–706.

Müller et al., (1991) "Gonadal Development and Growth in 46,XX and 46,XY Individuals with P450scc Deficiency (Congenital Lipoid Adrenal Hyperplasia)" *Horm. Res.* 36:203–208.

Sugawara et al., (1995) "Human Steroidogenic Acute Regulatory Protein: Functional Activity in COS–1 Cells, Tissue–Specific Expression, and Mapping of the Structural Gene to 8p11.2 and a Pseudogene to Chromosome 13" *Proc. Natl. Acad. Sci. USA* 92:4778–4782.

Pang et al., (1992) "Inherited Congenital Adrenal Hyperplasia in the Rabbit: Absent Cholesterol Side–Chain Cleavage Cytochrome P450 Gene Expression" *Endocrinology* 131(1):181–186.

Izumi et al., (1993) "Prenatal Diagnosis of Congenital Lipoid Adrenal Hyperplasia" *Obstetrics and Gynecology* 81(5):839–841.

Stocco et al., (1991) "The 30–kDa Mitochondrial Proteins Induced by Hormone Stimulation in MA–10 Mouse Leydig Tumor Cells Are Processed from Larger Precursors" *J. Biol. Chem.* 266(29):19731–19738.

(List continued on next page.)

*Primary Examiner*—W. Gary Jones
*Assistant Examiner*—Ethan Whisenant
*Attorney, Agent, or Firm*—Cooley Godward LLP

[57] ABSTRACT

Method for diagnosis of congenital lipoid adrenal hyperplasia and for the detection of the presence of a mutated gene for steroidogenesis acute regulatory protein (StAR) by analyzing nucleic acid obtained from a patient. The nucleic acid can be analyzed by restriction fragment length polymorphism analysis, nucleic acid hybridization, or nucleotide sequencing, among other techniques. A mutation may result in premature termination of the protein, or it may result in the StAR gene not being transcribed or translated, or it may result in a change in the amino acid sequence of the StAR gene product.

9 Claims, 14 Drawing Sheets

PUBLICATIONS

Yang et al., (1993) "Inherited Congenital Adrenal Hyperplasia in the Rabbit is Caused by a Deletion in the Gene Encoding Cytochrome P450 Cholesterol Side–Chain Cleaveage Enzyme" *Endocrinology* 132(5):1977–1982.

Camacho et al., (1968) "Congenital Adrenal Hyperplasia Due to a Deficiency of One of the Enzymes Involved in the Biosynthesis of Pregnenolone" *J. Clin. Endocr.* 28:153–161.

Kirkland et al., (1973) "Congenital Lipoid Adrenal Hyperplasia in an Eight–Year–Old Phenotypic Female" *J. Clin. Endocrinol. Metab.* 36:488–496.

Solish et al., (1988) "Human Adrenodoxin Reductase: Teo mRNAs Encoded by a Single Gene on Chromosome 17cen→q25 are Expressed in Steroidogenic Tissues" *Proc. Natl. Acad. Sci. USA* 85:7104–7108.

Miller et al., (1987) "Molecular and Clinical Advances in Congenital Adrenal Hyperplasia" *The Journal of Pediatrics* 111(1):1–17.

Lin et al., (1995) "Role of Steroidogenic Acute Regulatory Protein in Adrenal and Gonadal Steroidogenesis" *Science* 267:1828–1831.

Harikrishna et al., (1993) "Construction and Function of Fusion Enzymes of the Human Cytochrome P450scc System" *DNA and Cell Biology* 12(5):371–379.

Chung et al., (1986) "Human CHolesterol Side–Chain Cleavage Enzyme, P450scc: cDNA Cloning, Assignment of the Gene to Chromosome 15, and Expression in the Placenta" *Proc. Natl. Acad. Sci. USA* 83:8962–8966.

Picado–Leonard et al., (1988) "Human Adrenodoxin: Cloning of Three cDNAs adn Cycloheximide Enhancement in JEG–3 Cells" *J. Biol. Chem.* 263:3240–3244.

Black et al., (1994) "The Mitochondiral Environment is Required for Activity of the Cholesterol Side–Chain Cleavage Enzyme, Cytochrome P450scc" *Proc. Natl. Acad. Sci. USA* 91:7247–7251.

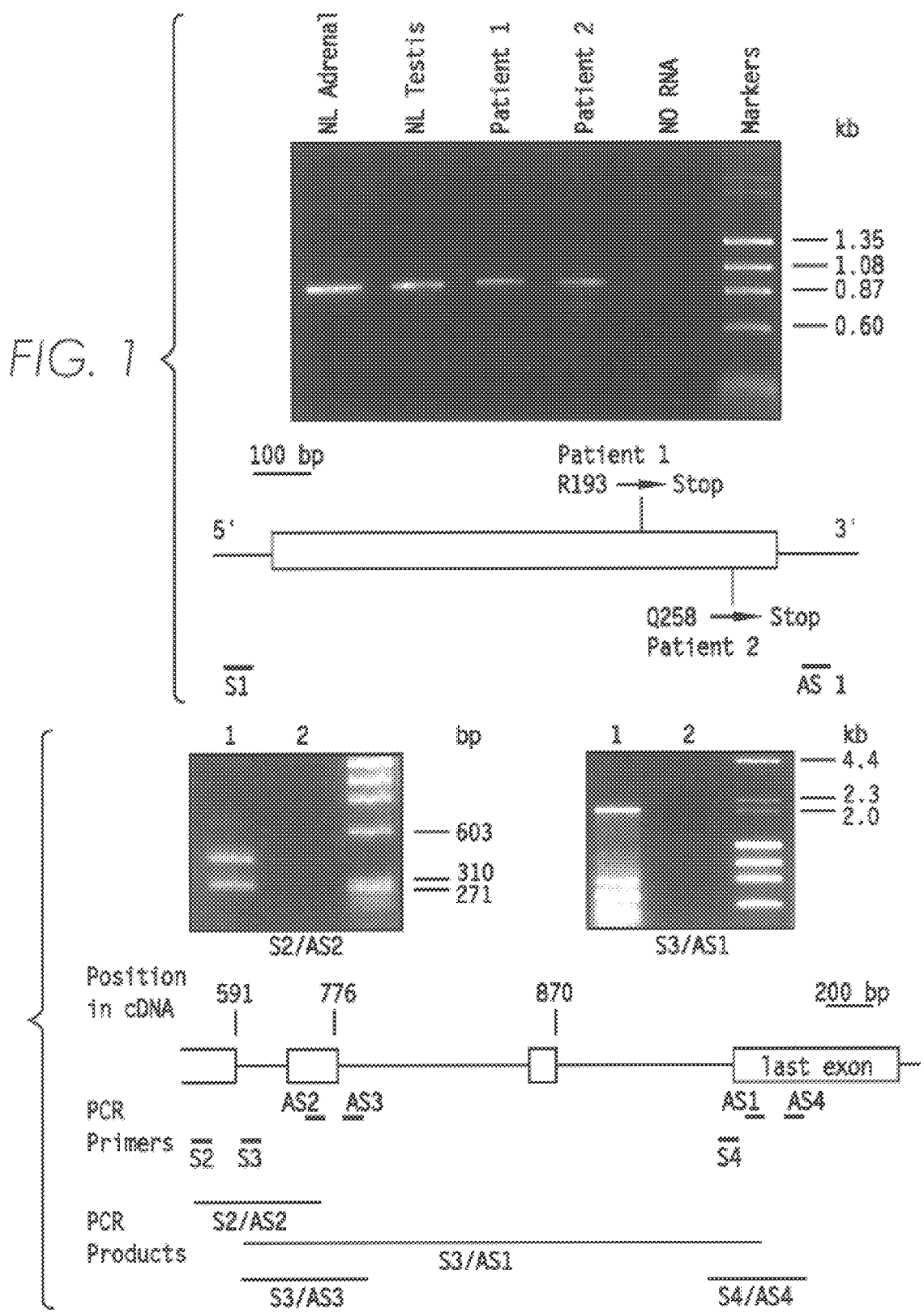

FIG. 4A

CCA CGC GTC CGC GAA GCT TGA GGG GCT CAG GAA GGA CGA AGC AAC CAC CCT TGA GAG AAG AGG CAG CAG CGG CAG CAC CAG CGG CAG CCC CAC CAC ATT TGC CAG
                                                                                                                                         20                          40                          60                          80                         100                         120

GAA ACA ATG CTA GCG ACA TTC AAG CTG TGC CTG GGG AGC TCC AGA CAC TAC AGA CGC AAC ATG AAG GGG AGG CAA CAG GCT GTG ATG GCC ATC AGC CAG CAG AGG
Met Leu Ala Thr Phe Lys Leu Cys Ala Gly Ser Ser Arg His Tyr Arg Arg Asn Met Lys Gly Arg Gln Gln Ala Val Met Ala Ile Ser Gln Gln Arg>
                         140                         160                         180                         200                         220                         240

GCC CTG GGG GGC CCC ACC CCT AGC ACG TGG ATT AAC CAG GTT CGG CGG AGC TCT CTA CTC GGT TCT CGG CTG GAA GAG ACT CTC TAC AGT GAC CAG GAG CTG CAG
Ala Leu Gly Gly Pro Thr Pro Ser Thr Trp Ile Asn Gln Val Arg Arg Ser Ser Leu Leu Gly Ser Arg Leu Glu Glu Thr Leu Tyr Ser Asp Gln Glu Leu Gln>
                         260                         280                         300                         320                         340                         360

GGG GAG GAG GCC ATG CAG AAG GCC TTG GCC ATC CTT AGC AAC CAA GAG GGC AAG GAG AGT CAG GAC AAT GGG GAC AAA GTG AGT ATG AGT GTC CCA GAT GTG GGC AAG
Gly Glu Glu Ala Met Gln Lys Ala Leu Ala Ile Leu Ser Asn Gln Glu Gly Lys Glu Ser Gln Asp Asn Gly Asp Lys Val Ser Met Ser Val Pro Asp Val Gly Lys>
                         380                         400                         420                         440                         460                         480

GTG TTC CGG CTG GAG GTC GTG GTG GAC CAG CCC ATG GAG AGG CTC TAT GAA GAG CTC GTG GAG CGC ATG GAA GCA ATG GGG GAG TGG AAC CCC AAT GTC AAG GAG ATC AAG GTC CTG CAG
Val Phe Arg Leu Glu Val Val Val Asp Gln Pro Met Glu Arg Leu Tyr Glu Glu Leu Val Glu Arg Met Glu Ala Met Gly Glu Trp Asn Pro Asn Val Lys Glu Ile Lys Val Leu Gln>
                         500                         520                         540                         560                         580                         600

AAG ATC GGA AAA GAT ACA TTC ATT ACT CAC GAG CTG GCT GCC GAG GCA CCA AAC CTG GTG CCC CGT GAC TTT GTG AGC CGC GTG TGT GCC AAG CGC CGA GGC TCC ACC TGT GTG
Lys Ile Gly Lys Asp Thr Phe Ile Thr His Glu Leu Ala Ala Glu Ala Pro Asn Leu Val Pro Arg Asp Phe Val Ser Arg Val Cys Ala Lys Arg Arg Gly Ser Thr Cys Val>
                         620                         640                         660                         680                         700                         720

FIG. 4B

```
          740                760                780                800                820                840
CTG GCT GGC ATG GAC ACA GAC TTC GGG AAC ATG CCT GAG CAG AAG GGT GTC ATC AGG GCG GAG CAC GGT CCC ACT TGC ATG GTG CTT CAC CCG TTG GCT GGA AGT CCC TCT AAG ACC AAA
Leu Ala Gly Met Asp Thr Asp Phe Gly Asn Met Pro Glu Gln Lys Gly Val Ile Arg Ala Glu His Gly Pro Thr Cys Met Val Leu His Pro Leu Ala Gly Ser Pro Ser Lys Thr Lys>
          860                880                900                920                940                960
CTT ACG TGG CTA CTC AGC ATC GAC CTC AAG GGG TGG CTG CCC AAG AGC ATC ATC AAC CAG GTC CTG TCC CAG ACC CAG GAT TTT GCC AAC CAC CTG CGC AAG CGC CTG GAG TCC CAC
Leu Thr Trp Leu Leu Ser Ile Asp Leu Lys Gly Trp Leu Pro Lys Ser Ile Ile Asn Gln Val Leu Ser Gln Thr Gln Asp Phe Ala Asn His Leu Arg Lys Arg Leu Glu Ser His>
          980                1000               1020               1040               1060               1080
CCT GCC TCT GAA GCC AGG TGT TGA AGA CCA GCC TGC TGT TCC CAA CTG TGC CCA GCT GCA CTG GTA CAC ACG CTC ATC AGG AGA ATC CCT ACT GGA AGC CTG CAA GTC TAA GAT CTC CAT
Pro Ala Ser Glu Ala Arg Cys ...>
          1100               1120               1140               1160               1180               1200
CTG GTG ACA GTG GGA TGG GTG GGG TTC GTG TTT AGA GTA TGA CAC TAG GAT TCA GAT TGG TGA AGT TTT TAG TAC CAA GAA AAC AGG GAT GAG GCT CTT GGA TTA AAA GGT AAC TTC ATT
          1220               1240               1260               1280               1300               1320
CAC TGA TTA GCT ATG ACA TGA GGG TTC AGG CCC CTA AAA TAA TTG TAA AAC TTT TCT GGG CCC TTA TGT ACC CAC CTA AAA CCA TCT ACA AGC AGA ATC CCT CTG CAG CCC TCT GCT CCT CCC
          1340               1360               1380               1400               1420               1440
GGG ATG CAT ACC ACA GGG CCT GAG AAG TCT TGG TTT ATG GGC TCA AGA ATG CCA TGC GCT GGC AGT ACA TGT GCA CAA AGC AGA ATC TCA GAG GGT CTC CTG CAG CCC TCT GCT CCT CCC
          1460               1480               1500               1520               1540               1560
GGC CGC TGC ACA GCA ACA CCA CAG AAC AAG CAG CAC CCC ACA GTG GGT GCC TTC CAG AAA TAT AGT CCA AGC TTT CTC TGT GGA AAA AGA CAA AAC TCA TTA GTA GAC ATG TTT CCC TAT
          1580               1600
TGC TTT CAT AGG CAC CAG TCA GAA TAA AGA ATC ATA ATT CAC ACC AAA AAA AAA AAA A
```

FIG. 8B
FIG. 9
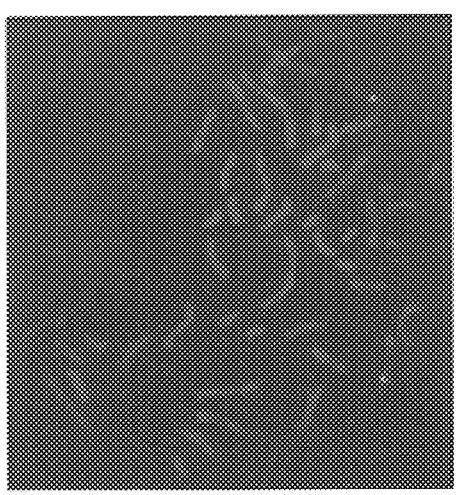
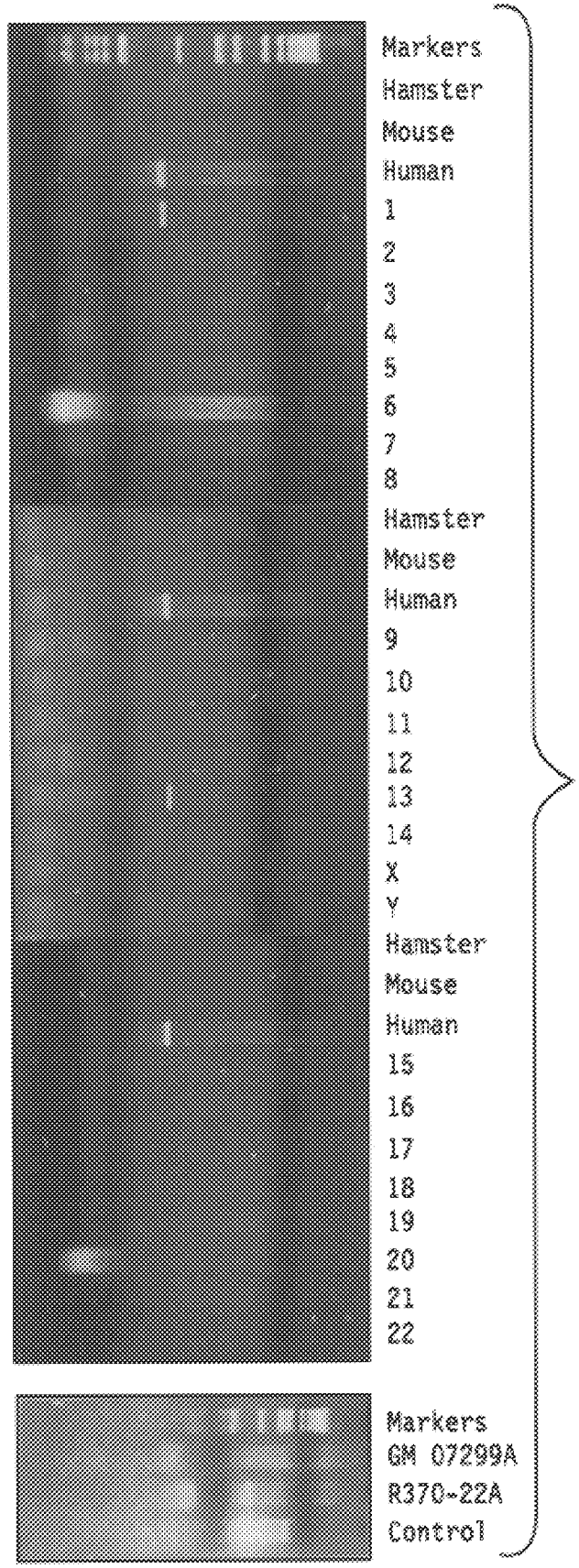

FIG. 10A-1

```
                                                                        [mRNA SEQ. POS.]
gcccccccccnaccagnactccaaanaccaacctcatgangcttggaggggttcanaa
aagtgagaanaattgacagttgaaaaccaactcctgggcccaggaggacctntgaaag
atgcttgaggccaagagctgggttgttgtactggccctnccactggccagctgtttgacc
cttgaccaatcaagtnccactctgtggactttcaggtctcacctctgcagggtcctggacttctca
catatgtctctactgcctggtaaacacacctgctcactctcgcgagatggtggttctca
aagtgtagtgtgtaccacaacaccacctgcattgcaaccactgggtatttattta
tttattttaattttattattatgatggagtctcactctgtcgcccagagtggatgcagt
ggcacgatcttggcttactgcaacctctgcctcctggccacatcaccggctaattttttgtatt
gcctccgagtagctggactacaggtgcctgccacatcaccggcttncgacgntcgacctcaagt
tttagtagagatgaggnntcnccatgttgcangctggttncgacgnctgacctcaagt
gatctgccaccncggccctnccaaagtgctgggnntaaaggcgtaaaccaacgccctggc
caagggagnttttttcttttcgtttntcntnttttcnttcttttcctnctnntttt
ttnggtnttnntttttttnntaacacaggtttctgagcctcaattcagatcagctgagc
ctggagtttctgnagacaagggctagaaatctgcacttttaaagtcttgaaaaccnctgtg
tgcctttcatctaagctgcccctgctctctctcctccatccctgcctgccctgtcctc
ctactctccctgcacctccccccgcccaagctccccacaaacgctcccacaaagcagcagt
gtgaggcaatcgctctatcctttgaccccntccctnnacagtgagtgntggcgnttttan
ctcctgatgatgatgcacancntcaccgggggnnagntaagacgcagaacaccaggtcc
aggctncagctgcggga
CTCAGAGGGCGAAGCTTGAGGGGCTCAGGAAGGACGAAGAACCACCCTTGAGAGAAGAGGC      60
AGCAGCAGCGGGCAGCAGCGGGCAGCAGCGGCGACCCCACTGCCACATTTGCCAGGAAA      120
CAATGCTGCTAGCGGACATTCAAGCTGTGCGCTGGGAGCTCCTACAGACACATGCGCAACA    180
TGAAGG
gtgagcgctgcgggaaggaggcgatgaggggtttggccagctctcagcgagtctgaggctcag
gccacccaattctgatcctagttgtgcctcttactggtgaacctgggcaagttcttcc
```

FIG. 10A-2

```
cttcttgaatctcagttttcccctcggaag                              [2 kb]
ggagcactaccatgggagntgaggtnctggctctagttcaggtccctgctagaatactgt
gttntnntgagcaagncacatccctctccacncccacttactcatttgagantanatgan
ggggtggngtgggccatctctaaggggcttngccagctcctagacaanggntattccctt
ctccag
        GGCTGAGGCAACAGGCTGTGATGGCCATCAGCCAGGAGCTGAACCGGAGGGCCC  240
TGGGGGGCCCCACCCCTAGCACGTGGATTAACCAGGTTCGGCGGCGGAGCTCTCTACTCG  300
gtaagtgctgaggcttctgggctcctggtgctgctggcaggaggttccctggagggtgat
gtggtgcatgtggctttggctcccctcctgccattccttcattttgagaggacgtcccca
gcctagagttcctcaaggccagatccctctctggtcacctggggcggctgtgattaactc
gaccagcaggctggccccatggctttagtccgggctcttcagagcaatgagcagaccca
gagctccagggatgagagctggtggaggctgggagaagaaggaagctctgtctctcctcg
gatgtgtatccag
        GTTCTCGGCTGGAAGAGACTCTCTACAGTGACCAGGAGCTGGCCTATCTCCAGCAGGGGG  360
AGGAGGCCATGCAGAAGGCCTTGGGCATCCTTAGCAACCAAGAGGGCTGGAAGAAGGAGA  420
GTCAGCAG
gtaagtgtcggggagaagcctgtggttcctccat                          [2 kb]
atgcccggccaagaatattttgtctaaccaccttctgggggctccttcctctgacag
        GACAATGGGGACAAAGTGATGAGTAAAGTGGTCCCAGATGTGGGCAAGGTGT  480
TCCGGCTGGAGGTCGTGGTGGACCAGCCCATGGAGAGGCTCTATGAAGAGCTCGTGGAGC  540
GCATGGAAGCAATGGGGGAGTGGAACCCCAATGTCAAGGAGATCAAG
gtgagcaaagtccaggtgcgggtggcaggggcccaggagagcccagtgtgaatgctgtat
caaagagaggacccctagctgtgggggtgcttagcccaacacaggctgagtcgtgattc
tggttccccatggcctggtag
                        GTCCTGCAGAAGA  600
TCGGAAAAGATACATTCATTACTCACGAGCTGGCTGCCGAGGCAGCAGGAAACCTGGTGG  660
GGCCCCGTGACTTTGTGAGCGTGCGCTGTGCCAAGCGCCGAGGCTCCACCTGTGTGCTGG  720
CTGGCATGGACACAGACTTCGGGAACATGCCTGAGCAGAAGGGTGTCATCAG
gtaatacgggcagcaggctccaaaccccc.........................
...............naggantccccactttccncctnacctnacnttccccaatttccag
                                                    GGCGGAGC  780
ACGGTCCCACTTGCATGGTGCTTCACCCGTTGGCTGGAAGTCCCTCTAAGACCAAACTTA  840
CGTGGCTACTCAGCATCGACCTCAAG
```

FIG. 10B

```
gtgaagggcatgggagggggacctggaaggcaggt                          [0.4k]
tatgnganagggtgcagantcaancntggtgcatagnccacaagatgagcacattctcct
accacctactgaag
                          GGGTGGCTGCCCAAGAGCATCATCAACCAGGTCC   900
TGTCCCAGACCCAGGTGGATTTTGCCAACCACCTGCGCAAGCGCCTGGAGTCCCACCCTG   960
CCTCTGAAGCCAGGTGTTGAAGACCAGCCTGCTGTTCCCAACTGTGCCCAGCTGCACTGG  1020
TACACACGCTCATCAGGAGAATCCCTACTGGAAGCCTGCAAGTCTAAGATCTCCATCTGG  1080
TGACAGTGGGATGGGTGGGGTTCGTGTTTAGAGTATGACACTAGGATTCAGATTGGTGAA  1140
GTTTTTAGTACCAAGAAAACAGGGATGAGGCTCTTGGATTAAAAGGTAACTTCATTCACT  1200
GATTAGCTATGACATGAGGGTTCAGGCCCCTAAAATAATTGTAAAACTTTTTTTCTGGGC  1260
CCTTATGTACCCACCTAAAACCATCTTTAAAATGCTAGTGGCTGATATGGGTGTGGGGGA  1320
TGCTAACCACAGGGCCTGAGAAGTCTTGCTTTATGGGCTCAAGAATGCCATGCGCTGGCA  1380
GTACATGTGCACAAAGCAGAATCTCAGAGGGTCTCCTGCAGCCCTCTGCTCCTCCCGGCC  1440
GCTGCACAGCAACACCACAGAACAAGCAGCACCCCACAGTGGGTGCCTTCCAGAAATATA  1500
GTCCAAGCTTTCTCTGTGGAAAAAGACAAAACTCATTAGTAGACATGTTTCCCTATTGCT  1560
TTCATAGGCACCAGTCAGAATAAAGAATCATAATTCACACC                    1601
aaacatcagtctttgttttaatattgtacttgttaaaaaaatctatgcagctgggtgcag
tggctcacgcctgtaatcccagcatttgggaggctgaggtaggcggatcgagtcgactc
cctttagtgagggttaattgagctccaccgcggtggcggccgctctagaactagtggatc
ccccgggctgcaggaattcgatatcaagcttatcgataccgtcgacctcgaggggggcc
cggtacccgga
```

FIG. 11A

```
GGATCTNTTCTATAGAAAACAAACTCAAGTGAGGTGGAAAATGATGATATTCTTCTAATA
AGAGAAAGCTCAGAAATCAGAGCTGNGAGAGTGAAACAGAAGGAAAGTTATGATNTANAG
ACGGGNNGGCATGATGTGATGAGAAGCGCATTTCACTTCTGTGGCATTGNCNTCTNAAAC
NTCATNCACTCCAGTNANNCATNNGACNCCAGNAGACCNNCCCCACACCTGAAGGATATT
CTACAAAATGTTTGATCAGTATAATTCAAAAGTGTCAAGCTTACAAAAAAATAAAGAGTG  300

AGAACTCATNNCTGGAGAACACTAGAAAANANTGCAACATGGNATCATAGATTAAATACT
GAAACAGAAAAANAGGATATTAATGGAAAAGCTGATAAANTCAGAATAAAGTCTGCAATN
TGATTCACAGCATCATACGANTGTGAATNTCTAAGTTGTGATAAGTGTTTCATGGNTGNC
TACANTGTNAACCTNAGAGAAACCTGAGTAAATGGTAAGAACTCNCTATAAAATNNGGCN
ACTATTCTGTAAATATCNAAATAATAATAATAAAGAGGAAATAGTAGCNAAACNAATGAA  600

AACNNGGGAGTAATACCAAGAGTGGAAATAAATTAAAATGGAACNAGGGGGACCAAACTA
CATAGACACAAATTAAANCTGCAACATNACCTAAATATTTCTTAAAGATATTAAGCTTTA
CATATAAAGATTATAGAAATNCATATCTACCTNGATTTTAATGACATAATGTGTATATTA
AGATTAATCTGGGTTGTTGNACATTTNCTGTATATTTCTGAATNGGCACATNGCCAGAAT
GAGTAACTGGCTTGGCATTATAATNAACTCCTGGAGAAATNTATTTAGAGGGAATAAAAC  900

AATATNTTNGGCTAAGNCATAGAATGGACAACTCAGNTATGCTTCAGGTNNTCTTAGTAG
GGAGTATGTGGGTGNGNGGGTGGCAGATAAGCCGCTCACATCCTAGGGTTAGACTTACTG
GGAAGATCCCNTGGGATCCGAAATGGAAGTCNAAGTTTCTGTTATCNAATTTTNGTGACT
CCAAAAGGACCGGAAAGACCAGAGATAAGCACTAAATGAGAACNATAAATAAGCAAAAAG
GTGTGTCCTACCGATTTCAATATTCAGTGAGTCTATAAGAAGGACCTGAGCCATCGAGCC  1200

TGGCCAAAATATTGGATTCTAATTAAAGAGTAGAGTGAGGAGGGGCACAGAGGACAGCCT
CCAGGGGGAGGCCGCACTGCAAGCATCCCTGGAGTGGCGAAGGTATGCACTGGATGGATG
GCAGCAGGCGCTGCACGGGGGAGCTGAGCACTGCCAGGAAGAATCCAGTGAGTGATGGCG
TTTATCTCTCCTGATGATGATTCACAGCCTTCAGTGGGGACATTTAATACGTGGAACAC
CGGGTCCAGGCTGCAGCTGCGGGACTCAGAGGCAAAGCTTGAGTGNCTCAGGAAGGACGA  1500

AGAACCACCCTTGAAAGAAGAGGCAGCCTCACCGGCGTTGGCGGCCCCACCACTGCCACA
TCTGCCAGGAAAGATGCTGCTAGCGACATTCAAACTGTGCTCCAGGAGCTCCTACAGACA
CATGCGCAACATGAAGGGGCTGAGGCAACAGGCTGTGAGGGGGCATCGGGCAGGAGCTTA
ACCGGAGGGCCCTGGGGGCCCCACCCCAAGCGCTTGGATTAACCAGGTTCCGCGGCGGAG
CTCTCTGCTTCGTTCTCTGCTGGAAGAGACTCTCTACCCGGGTGCGGTGGCTCACGCCTG  1800
```

FIG. 11B

```
TAATACTAGCACGTTGGGGGGCCGAGGCGGGCAGATCATGAGGTTAGGAGTTCGAGAGCA
GNCCGACCCACATGGTGAAACCCCATCTCTACTAAAAATACAAAAATTAGCTGGGAGTGG
TGGTGCGGGGCCTGTAATCCCAACTACTCAGGAGGCTGAGGCAGGAGAATCGCTTGAACT
CGGGGACGGGGGGGNGGGCGGGGAAAGACTCTCTACAGTGACCAGGAGCTGACCTATCTC
CANCAGTGGGGAGGAGNCCATNCAGAAGNCCTTGGGCATCCTTAGCCCTCGCCANCTACG  2100

AGGGCTGGAAGAAGGAGAGCCACCAGGACAATGGGGATAAAGTGATGAGTAAAGTGGTTC
CAGATGGGGCAAGGTGTTCCGNCTGGAAGTCGTGGTGGACCANCCCATGGAGAGGCTCTA
CANAGAGCTCGTGGAGTGCATGGAGGCAATGGGGGAGTGCAACTCCAATATCAAGGCGAT
CAAGGTCTTGCAGAAGATGATCAGAAAAGATACATTCATTGCCCATGAGCTGGCTGCAGA
GGCAGCAGGAAACCTAGTGGGGCCTTGTGACTCTGTGAGCATGTGCTGTGCCAAGCGTCA  2400

AGGCTCCACCTGTGTTGCTGGCTGGCATGGCCACAGACTTCGGGAACATGCCCGAGCAGA
AGGGTGTCATCAGGGGGAGCATGGTCCCACTTGCATGGTGCTTCACCTGGTGACTGGAAG
TCCCTCCAAGACCAAACTTACATGACTGCTCAGCATCGACCTCAAGGGGTGGCTTCCCAA
GAGCATCATCAACCAGGTCCTGTCCCAGACCCAGGTGGATTTTGCCAACCACCTGCACAA
GCGCCTGGAGTCCCACCCTGCCTCTGAAGCCAGGTGTTGAAGGCCAGCCTGCTGTTCCCA  2700

AGTGTGTCCAGCTGCACTGCTACACACGCTTATCAGGAGAATCCTTGCTGGAAGCCTGCA
AGCTTAAAATCTCCATCTGGCGACAGAGGAATAGGTGGGGTTAGTGTATAGAGTATGATA
CTAGGATTCAGACTGGTAAAAGTTTTTAGTACCAAGAAAACAAGGATGAGGCTCTTTGAT
TAAAAGGTAACTTCATTCACTGACTAGCTATGACATGAAGGTTGAGGATCCTAAAATAAT
TGTAAAACTTTTTTTNCTGGGCCTTTATGTGNCCACCTAAAACCATCTTTAAAATGCTAG  3000

TGGCTGATATGTGTGGGGGGATGCTAGTCACAGGGCCTGAGGAGTCTTGCTTTATGGGCT
GGAGNACCCCATTCCCTGGAGGCAGAGCATGTTCACCAAGCAGNATCTTAGAGGGTCTCC
TNCAGCCCTCCACTCCNCCAANTCGCTNCATGGCNACACCAGATAACAANCAGCACCCCN
CAGTGGGTACCTTCCAGAAANATAGTCCNAGCTTTCTCTATGGGAAAAGACCNANCTAAT
TAGTAAATAGGTTTCCCTATTGAGTCCATAGGCACCAGTCAGAGAAAAGAATCATAATTC  3300

ACACACACACACACACACACACACACACACACACNACCAGGACCTGAGTTCAGAAAATGA
AGCCTGTAATCACACACTAAAATGAAAACAATAAATCATGTGTATTACAGTTAATAAATG
AATANNATGTATTGCTTCTATAGCCTTGTGATATGGTTTGGCTGTGTCTGCACCCAAATC
TCATCTT                                                       [3487]
```

IDENTIFICATION OF GENE MUTATIONS ASSOCIATED WITH CONGENITAL LIPOID ADRENAL HYPERPLASIA

ACKNOWLEDGEMENTS

This invention was supported in part by NIH Grants HD 06274, HD 07688, HD 17481, RR000847, DK 37922, and DK 42154. The U.S. Government has rights in this invention.

INTRODUCTION

TECHNICAL FIELD

This invention is directed to a genetic sequence that has been identified as the locus of mutations that cause congenital lipoid adrenal hyperplasia (lipoid CAH) and to methods for the diagnosis of this disease and for the detection of the presence of the mutated gene as an indication of potential for genetic transmission of the disease.

BACKGROUND

Steroid hormone synthesis is greatly increased in response to tropic hormone stimulation. Although increased transcription of genes encoding steroidogenic enzymes is important in the chronic hormonal response, the rate-limiting step in the acute response is the transport of cholesterol into mitochondria (J. F. Crivello et al., *J. Biol. Chem*, 255, 8144 (1980); C. R. Jefcoate et al., *J. Steroid Biochem*. 27, 721 (1987)). Several molecules have been proposed to participate in this transport, but their roles have not been definitively established.

Congenital lipoid adrenal hyperplasia (lipoid CAH) is an autosomal recessive disorder characterized by a severe deficiency of adrenal and gonadal steroid hormones (H. J. Degenhart et al., *Acta Endocrinol*. 71, 215 (1972); S. Koizumi et al., *Clin. Chem. Acta*. 77, 301 (1977); B. P. Hauffa et al., *Clin. Endocrinol*. 23, 481 (1985)). Affected infants die from salt loss, hyperkalemic acidosis and dehydration unless treated with steroid hormone replacement. XY genetic male patients are born with female external genitalia due to the absence of testicular testosterone synthesis. Since mitochondria from affected adrenals and gonads fail to convert cholesterol to pregnenolone, the disease was previously thought to be due to a defect in the cholesterol side chain cleavage enzyme, P450scc. However, the involvement of P450scc has been ruled out by molecular genetic analysis of affected individuals (D. Lin et al., *J. Clin. Invest*. 88, 1955 (1991); Y. Sakai et al., *J. Clin. Endocrinol. Metab*. 79, 1198 (1994)). We reasoned that the defect could involve the transport of the cholesterol into mitochondria (D. Lin et al., *J. Clin. Invest*. 88, 1955 (1991); D. Lin et al., *Genomics* 18, 643 (1993). However, prior to the current elucidation of a molecular defect for lipoid CAH, no specific defect had been found to be associated with this disease.

SUMMARY OF THE INVENTION

Accordingly, it is an object of the present invention to provide a genetic method of diagnosing congenital lipoid congenital hyperplasia in humans.

It is another object of detecting the presence of mutations in a gene responsible for congenital lipoid adrenal hyperplasia in humans for use in genetic counseling.

It is a further object of the invention to provide a method of treating congenital lipoid adrenal hyperplasia in humans by providing a protein that replaces defective proteins in a human with the disease.

These and other objects of the invention as will hereafter become more readily apparent have been accomplished by providing an isolated DNA or RNA molecule, wherein the molecule contains (1) a first sequence consisting of hStAR cDNA (SEQ ID NO:1), hStAR genomic DNA as set forth in FIGS. 10A-1, 10A-2, and 10B, or a hStAR pseudogene as set forth in FIGS. 11A and 11B; (SEQ ID NO:3)(SEQ ID NO:4)(2) a second sequence, wherein the second sequence is a subsequence of the first sequence at least 10 nucleotides in length; (3) a third sequence in which at least one nucleotide of the first or second sequence is replaced by a different nucleotide; or (4) a fourth sequence complementary to any of the first second, or third sequences; with the provisos that (1) if the molecule is an RNA molecule, U replaces T in the sequence of the molecule, (2) the third sequence is at least 95% identical to the first or second sequence, and (3) the second sequence is not present in mouse StAR cDNA. The invention also provides methods for detecting mutated StAR genes in humans, such mutations having been associated with congenital lipoid adrenal hyperplasia.

BRIEF DESCRIPTION OF THE DRAWINGS

The invention now being generally described, the same will be better understood by reference to the following detailed description of specific embodiments in combination with the figures that form part of this specification, wherein:

FIG. 1. Detection of nonsense mutations in patients' StAR cDNAs. (Top) RT-PCR products of StAR from normal (NL) human fetal adrenal and testicular RNAs, testicular RNAs of patients 1 and 2, and no RNA control displayed on a 1% ethidium bromide-stained agarose gel. The molecular size markers are HindIII-cleaved bacteriophage λ. (Bottom) Map of StAR cDNA. R193→Stop is the substitution of a Stop codon (TGA) for $Arg^{193}$ (CGA) and Q258→Stop is a Stop codon (TAG) for $Gln^{258}$. The open box represents the coding region of StAR cDNA. The small bars below the map indicate the PCR primers. The sequence of the sense primer S1 was 5'-GCAGCAGCAGCGGCAGCAG-3'(SEQ ID NO:5)(66–84, position in cDNA) and the antisense primer AS1 was 5'ATGAGCGTGTGTACCAGTGCAG-3'(SEQ ID NO:6)(1016–1037). The PCR program was 94° C. 45 sec; 64° C., 30 sec; 72° C., 60 sec for 30 cycles.

FIG. 2. PCR mapping of the StAR gene. (Top) Left panel; genomic PCR products amplified with primers S2/AS2 displayed on a 2% ethidium bromide-stained agarose gel. The molecular size markers are HaeIII-cleaved bacteriophage φx174. Right panel: genomic PCR products amplified with primers S3/ASI displayed on a 1% agarose gel. The molecular size markers are HindIII-cleaved bacteriophage λ. In both gels, genomic DNA was either added as a template in PCR (lane 1) or not added (lane 2). (Bottom) Map of the 3' half of the StAR gene. Open boxes represent exons, and numbers labeled at the end of each exon are the corresponding nucleotide position in cDNA sequence (B. J. Clark, J. Wells, S. R. King, D. M. Stocco, *J. Biol. Chem*. 269, 28314 (1994)). Locations of the various PCR primers and products are shown below the map. The sense primer S2 was 5'GACAAAGTGATGAGTAAAGTG-3'(SEQ ID NO:7) (442–462) and antisense primer AS2 was 5'-TGTGGCCATGCCAGCCAGCA-3'(SEQ ID NO:8) (717–738). The PCR program using S2/AS2 was 94° C., 45 sec; 58° C., 30 sec; 72° C., 60 sec for 35 cycles. The sense primer S3 was 5'-GTGAGCAAAGTCCAGGTGCG-3' (SEQ ID NO:9). The PCR program using S3/ASI was 94° C., 50 sec; 64° C., 30 sec; 72° C., 90 sec for 35 cycles.

(FIG. 3A) (Top) Direct PCR sequencing (method of Dynal, Inc., Lake Success, N.Y.) from a normal control, patient 1, and parents of patient 1. Arrows indicate the nucleotide involved in the nonsense mutation: C in control, T in patient 1, C and T in both parents. (Bottom) DNA and amino acid sequences. (FIG. 3B) Direct PCR sequencing of a normal control, patient 2 and patient 3. Arrows indicate a C in the control and a T in both patients 2 and 3. In (FIG. 3A), the sense PCR primer (S3) was described in FIG. 2 and the biotinylated antisense primer (AS3) was 5'GGATGCAGTCCACATGCTTGG-3'(SEQ ID NO:10). The PCR program was 94° C., 45 sec; 64° C., 30 sec; 72° C., 45 sec for 35 cycles. A sense primer, 5'GATACATTCATTACTCAC-3'(SEQ ID NO:11) (613–630) was used for sequencing. In (FIG. 3B), the sense biotinylated primer (S4) was 5'-CCTGGCAGCCTGTTTGTGATAG-3'(SEQ ID NO:12) and the antisense (AS4) primer was 5'-CCTCATGTCATAGCTAATCAGTG-3'(SEQ ID NO:13) (1201–1223). The PCR program was 94° C., 45 sec; 63° C., 30 sec; 72° C., 45 sec for 35 cycles. Antisense primer AS1 was used for direct sequencing.

FIG. 4. FIGS. 4-A and 4-B show the nucleotide and deduced amino acid sequence (SEQ ID NO:1 and SEQ ID NO:2, respectively) of the human StAR cDNA (hStAR DNA). The potential sites for protein kinase A and protein kinase C-mediated phosphorylation are noted with single and double underlining, respectively.

FIGS. 8A and 8B.

FIG. 8A. Regional mapping of the StAR gene to 8p by somatic cell hybrid mapping. The chromosome 8 idiogram is modified according to Francke (Francke, U. (1994) Cytogenetics and Cell Genetics 65: 206–219). The right side of the idiogram shows a diagrammatic representation of the portion of human chromosome 8 present in the respective cell lines. The precise localizations of the boundaries of these DNAs on the cytogenetic map of the chromosome are approximate. The StAR, LPL, SS and CL1 genes were localized by PCR. Presence of a gene is denoted by a '+' and its absence by a '−' symbol. A negative control cell line, CHO-K1, which contains only hamster DNA was also included in these experiments (data not shown). The localization of LPL, SS and CL1 are consistent with previously published data (Wion, K. L., Kirchgessner, T. G., Lusis, A. J., Schotz, M.c., Lawn, R. M. (1987) Science 235: 1638–1641; Fink, T. M., Zimmer, M., Tschopp, J., Etienne, J., Jeene, D. E., Lichter, P. (1993) Genomics 16: 526–528; Schechter, I., Conrad D. G., Hart, I., Berger, R. C., McKenzie, T. L., Bleskan, J., Patterson, D. (1994) Genomics 20: 116–118).

FIG. 3B. YAC FISH localization of the StAR functional gene locus to 8p11.2. YAC DNA was nick translated with biotin dUTP and dCTP and hybridized with metaphase spreads with 1 $\mu$g yeast DNA/slide as described in the text. The probe was detected with avidin-FITC (yellow) and chromosomes were counter-stained with propidium iodide (red). The arrow to the left of the idiogram in panel A indicates the FISH location of the A 10 G5 YAC to the 8p11.2 region.

FIG. 9. Assignment of StAR pseudogene to human chromosomes 13. PCR analysis of somatic cell hybrid DNA was carried out with primers specific for the StAR pseudogene. The numbers above the lanes in the left hand panel refer to the hybrids analyzed in FIG. 7. Hybrid "1" (GM 10880) contains human chromosomes 1 as well as 13 and 14. Hybrid GM 07299A contains human chromosomes X and 1. R370-22A contains human chromosomes 1 and 13. The hybrid designated "13" contains only human chromosome 13. Control designates the cloned pseudogene sequences in pBluescript (Stratagene, La Jolla, Calif.). The 800 nt StAR pseudogene amplification product is seen only in hybrids containing human chromosome 13.

FIGS. 10A and 10B.

FIG. 10. FIGS. 10A-1, 10A-2, and 10B show the genomic and cDNA sequence (SEQ ID NO:3) of human StAR DNA. In accordance with standard conventions, the transcribed messenger (i.e., the cDNA) is shown in upper-case letters, with the 5' and 3' genomic sequences and the introns being shown in lower-case letters. For the purposes of this invention, a preferred specific subsequence of genomic DNA is a subsequence of the genomic sequence as set forth in this Figure (i.e., a preferred subsequence does not include the unsequenced sections of DNA omitted from the Figure, although such sequences can readily be determined by sequencing using standard techniques). Preferred subsequences also are those that do not contain unknown nucleotides (designated "N" in the Figure), although such nucleotides can be readily identified by re-sequencing the molecule of the invention.

FIGS. 11A and 11B.

FIG. 11. FIGS. 11A and 11B show the human StAR pseudogene cDNA (SEQ ID NO:4). The splicing error that results in this pseudogene is shown in FIG. 12.

DESCRIPTION OF SPECIFIC EMBODIMENTS

Figure 3A:
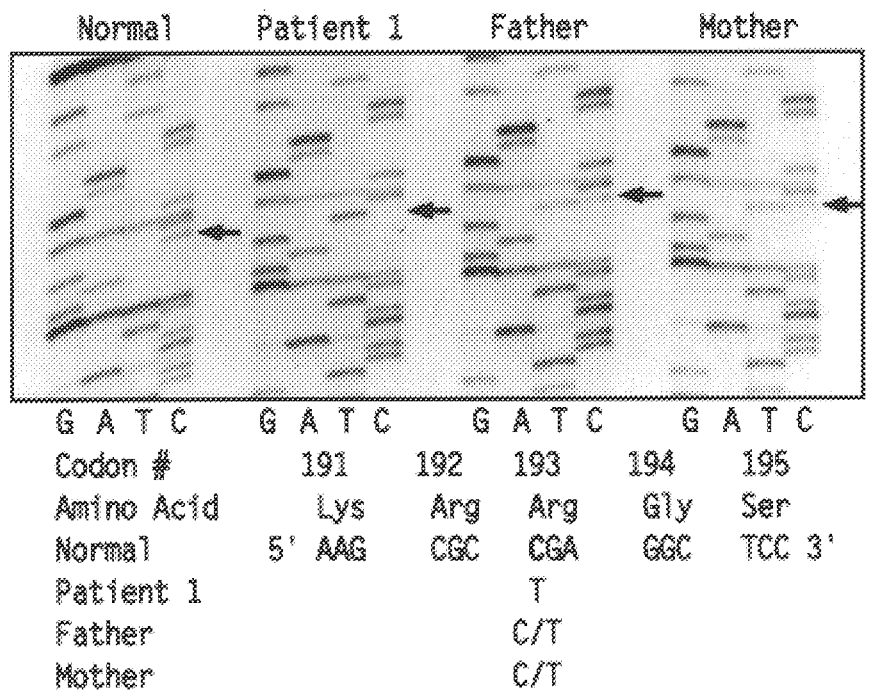
FIGS. 3A and 3B. Direct sequencing of PCR products.

The present invention arose in the context of investigations based on the prior indication that placental progesterone synthesis is necessary for the maintenance of pregnancy (J. F. Strauss III et al., in *Endocrinology*, L. J. DeGroot, Ed. (W. B. Saunders, Philadelphia, 1995), vol. 3, pp. 2171–2206). Since pregnancies with a lipoid CAH fetus progress normally to term and the placenta can still produce progesterone (P. Saenger et al., *J: Clin. Endocrinol. Metab.* 80, 200–205 (1995)), we speculated that the factor sought is required for adrenal and gonadal, but not placental, steroidogenesis. A recently described 30-kDa phosphorylated protein is believed to mediate the rapid and cycloheximide-sensitive response of steroidogenesis to tropic stimulation (D. M. Stocco and T. C. Sodeman, *J. Biol. Chem.* 266, 19739 (1991); L. F. Epstein and N. R. Orme-Johnson, *J. Biol. Chem.* 266, 19739 (1991); D. M. Stocco and M. Ascoli, *Endocrinology* 132, 959 (1993)). This protein, termed steroidogenesis acute regulatory protein (StAR), was purified from MA-10 murine Leydig tumor cells. The cloning of StAR cDNA from mouse was previously described in the scientific literature (B. J. Clark, J. Wells, S. R. King, D. M. Stocco, *J. Biol. Chem.* 269, 28314 (1994)). In order to determine whether our hypothesis was correct, i.e., that a genetic defect in this protein could be responsible for lipoid CAH, we cloned human StAR cDNA.

Transient expression of mouse StAR cDNA in MA-10 cells and COS-1 cells results in enhanced steroidogenesis (B. J. Clark, J. Wells, S. R. King, D. M. Stocco, *J. Biol. Chem.* 269, 28314 (1994)). We discovered similar properties for human StAR cDNA and further found that StAR mRNA is abundant in adrenal and gonad tissue, but not in placenta. Thus StAR appeared to be a good candidate for the factor involved in lipoid CAH. This prompted us to examine the StAR gene in three unrelated patients. Patient 1, of Caucasian ancestry, has not been reported previously. Patient 2, an ethnic Korean, and Patient 3, an ethnic Japanese, were previously described, but not with regard to the relevance of the StAR gene (Patient 3: B. P. Hauffa et al., *Clin. Endocrinol.* 23, 481 (1985).; Patients 2 and 3: D. Lin et al., *J. Clin. Invest.* 88, 1955 (1991); Patient 2: D. Lin et al., *Genomics* 18, 643 (1993).

We generated StAR cDNA from patients 1 and 2 by reverse transcription-polymerase chain reaction (RT-PCR) using testicular mRNA as template. When PCR primers from the 5' and 3' untranslated regions were used, the principal product was StAR cDNA, but there were related species that contained a large number of sequence differences. This lead to the discovery of a StAR pseudogene reported in the examples below. Using a sequence termed S1 in the 5' untranslated region that distinguishes authentic StAR from its pseudogene, we amplified the 974-bp StAR cDNA in normal controls and in two patients (FIG. 1). These RT-PCR products were subcloned into pCRII vectors and sequenced. All patient clones from independent RT-PCR reactions were identical to the wild type sequence (SEQ ID NO:1) except for a C to T transition in codon 193 (Arg) in patient 1 and a C to T transition in codon 258 (Gln) in patient 2. These generated premature stop codons, leading to mutant proteins lacking 93 or 28 amino acid residues, respectively, from the C-terminus.

To confirm the identity of these mutations, we analyzed StAR genes from genomic DNA of our patients. Since the structure of the StAR gene was unknown, we first used PCR to obtain a genomic clone containing the exons harboring the mutations. This was done by using various combinations of sense and antisense primers derived from the cDNA sequences to amplify normal genomic DNA. As shown in FIG. 2, the primer pair S2/AS2 yielded two specific products of 437 bp and 290 bp. The sequence of the 437-bp fragment matches the cDNA sequence (SEQ ID NO:1) at both ends perfectly and contains a 141-bp intron in the middle, thus deriving from the StAR gene. The 290-bp fragment was from the StAR pseudogene, lacking the intron. Subsequently, an intronic primer termed S3 was used with primer AS1 for PCR, which yielded a 2.1-kb product (FIG. 2). Mapping and DNA sequencing of this fragment revealed that the sequences of the exons match perfectly with the cDNA and all intron/exon boundaries strictly follow the GT/AG rule. Thus the 2.1 kb fragment represents the 3' half of the StAR gene. The sequence information obtained from the 2.1-kb clone enabled us to make intronic primers to PCR-amplify the exons (FIG. 2).

Figure 3B:
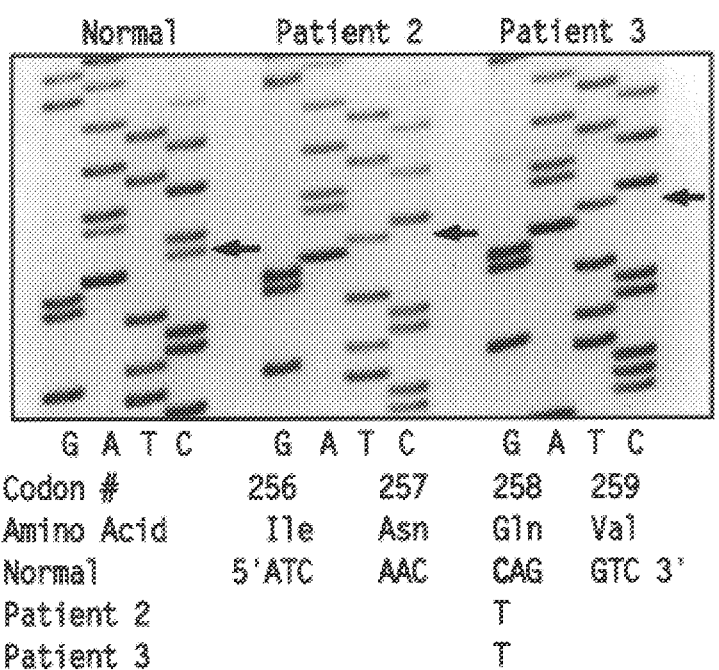

The presence of the nonsense mutations in codons 193 and 258 was confirmed by directly sequencing PCR products of the genomic DNA. As shown in FIG. 3A, patient 1 has a C to T transition at codon 193, whereas her father or mother have C and T at codon 193 (one on each of their two chromosomes). Therefore, we conclude that patient 1 is homozygous for the $\text{Arg}^{193} \rightarrow \text{Stop}$ mutation, and both of her parents are carriers for this mutation. Similarly, patient 2 is homozygous for the $\text{Gln}^{258} \rightarrow \text{Stop}$ mutation (FIG. 3B). As expected, the mother of patient 2 was heterozygous for this mutation, while a normal sibling had no mutation (not shown). In addition, patient 3 was homozygous for the same mutation as patient 2 (FIG. 3B); her mother is also a carrier. Since patient 2 is an ethnic Korean and patient 3 is an ethnic Japanese, this finding suggests a common origin for this mutation in these two ethnic groups.

To prove that these premature stop codons in StAR cause functional alterations, we analyzed the expressed wild-type and mutant proteins for their ability to enhance steroidogenesis. Using lipofectamine, nonsteroidogenic COS-I monkey kidney cells were transfected with pSPORT (Vector) or with pSPORT expressing normal human StAR or the mutant StAR from patients 1 and 2 (or 3). The cells were co-transfected with either vectors expressing bovine P450scc and bovine adrenodoxin (both provided by Dr. Michael Waterman, Vanderbilt University), or a pECE vector expressing a fusion protein termed F2, consisting of the human cholesterol side-chain cleavage system: $H_2N$-P450scc-Adrenodoxin Reductase-Adrenodoxin-COOH (J. A. Harikrishna et al., *DNA Cell Biol.* 12, 371 (1993)). The substrate was either the cellular and serum cholesterol (chol) or added 5 µg/ml 20α-hydroxycholesterol (20α). After 48 h of incubation, the medium was collected and assayed for pregnenolone by immunoassays. The results are shown in Table 1. Co-expression of StAR with the cholesterol side chain cleavage system resulted in an approximately eight-fold increase in pregnenolone production when cholesterol was used as a substrate. Both mutant StAR proteins are inactive, indicating that each of the two nonsense mutations causes lipoid CAH. Unlike cholesterol, 20α-hydroxycholesterol can readily diffuse into the mitochondria and thereby bypasses the mitochondrial cholesterol transport system (M. E. Toaff et al., *Endocrinology*, III 1785 (1982)). With 20α-hydroxycholesterol as a substrate, there are no significant differences in pregnenolone production between normal StAR and mutant StARs. The differential effects of StAR on utilization of cholesterol and 20α-hydroxylcholesterol strongly suggest that StAR mediates the transport of cholesterol into mitochondria.

TABLE 1

Loss of StAR activity due to nonsense mutations
Pregnenolone Production (ng/dish)

| Co-transfection | scc/Adx | | F2 | |
|---|---|---|---|---|
| | chol | 20α | chol | 20α |
| Vector | 20 ± 1 | 158 ± 21 | 17 ± 3 | 60 ± 7 |
| StAR | 175 ± 19 | 138 ± 15 | 131 ± 23 | 60 ± 11 |
| Patient 1 | 19 ± 2 | 99 ± 23 | 18 ± 5 | 56 ± 7 |
| Patient 2 or 3 | 25 ± 4 | 168 ± 35 | 22 ± 4 | 75 ± 7 |

Values are the means ± standard deviations from four separate transfections.

StAR is synthesized as a 285 amino acid protein with a mitochondrial targeting sequence of 25 residues, which is cleaved from the N-terminus following transport into mitochondria. The precursor and mature StARs have half-lives in the range of minutes and hours, respectively. Digital videoscanning of immunoblots (Clark et al. 1994) revealed that about 70% of StAR in COS-1 cells transfected with wildtype plasmid was in the mature form. However, no mature form was seen for mutant protein from patient 1 and about 10% was processed for patient 2 (not shown), suggesting a possible mechanism for the loss of activity.

Lipid CAH is the only known inborn disorder of steroid hormone synthesis not caused by a defective steroidogenic enzyme. The identification of mutant StARs in lipoid CAH now permits prenatal molecular diagnosis for this devastating disease. Lipoid CAH due to nonfunctional StARs is comparable to the effect of a StAR gene knockout, demonstrating that StAR is indispensable for adrenal and gonadal steroidogenesis. Thus, StAR is the first protein identified that plays an essential role for cholesterol access to P450scc. The sparing of fetuses with lipoid CAH as a result of the presence of normal placental steroidogenesis and the absence of StAR expression in placenta (as we discovered) and in other steroidogenic tissues, such as brain (P. Robel and E. E. Baulieu, *Trends Endocrinol. Metab.* 5, 1 (1994); S. H. Mellon, *J. Clin. Endocrinol. Metab.* 78, 1003 (1994)), suggests that different mechanisms may exist to facilitate cholesterol transport into mitochondria in these tissues. This demonstration of the critical role of StAR in lipoid CAH provides the first genetic evidence for the hypothesis that StAR is the long-sought molecule that mediates the acute tropic regulation of steroid hormone synthesis (D. M. Stocco and T. C. Sodeman, *J. Biol. Chem.* 266, 19739 (1991); L. F. Epstein and N. R. Orme-Johnson, *J. Biol. Chem.* 266, 19739 (1991); D. M. Stocco and M. Ascoli, *Endocrinology* 132, 959 (1993)).

Thus, the present invention provides an isolated DNA molecule, in which the molecule contains (1) a first sequence consisting of hStAR cDNA (SEQ ID NO:1), hStAR genomic DNA as set forth in FIGS. 10A-1, 10A-2, and 10B, or hStAR pseudogene as set forth in FIGS. 11A and 11B; (SEQ ID NO:3), (SEQ ID NO:4), (2) a second sequence, wherein the second sequence is a subsequence of the first sequence at least 10 nucleotides in length; (3) a third sequence in which at least one nucleotide of the first or second sequence is replaced by a different nucleotide; or (4) a fourth sequence complementary to any of the first second, or third sequences; with the provisos that (1) if the molecule is an RNA molecule, U replaces T in the sequence of the molecule, (2) the third sequence is at least 95% identical to the first or second sequence, and (3) the second sequence is not present in mouse StAR cDNA. Any of these sequences can be used in the identification of the presence (or absence) of a mutation in the StAR gene of a human and thus can be used in the genetic counseling of individuals, for example those with a family history of congenital lipoid adrenal hyperplasia (although the general population can be screened as well). In particular, it should be noted that the invention is not limited to use or identification of the specific mutations that have already been identified. Any mutation in the StAR gene away from the normal gene sequence identified here is an indication of a potentially fatal genetic flaw, even so-called "silent" mutations that do not encode a different amino acid at the location of the mutation are potential disease mutations, since such mutations can introduce into (or remove from) the gene an untranslated genetic signal that interferes with the transcription or translation of the gene. Since one of the utilities based on the gene sequences identified here is in genetic counseling of families with a history of lipoid CAH, advice can be given to a patient concerning the potential for transmission of lipoid CAH if any mutation of the StAR gene is present. While an offspring with the mutation in question may or may not have symptoms of lipoid CAH, patient care and monitoring can be selected that will be appropriate for the potential presence of the disease; such additional care and/or monitoring can be eliminated (along with the concurrent costs) if there are no differences from the normal gene sequence. As additional information (if any) becomes available (e.g., that a given silent mutation or conservative replacement mutation does or does not result in lipoid CAH), the advice given for a particular mutation may change. However, the change in advice given does not alter the initial determination of the presence or absence of mutations in the StAR gene that this invention has for the first time indicated to be a sufficient cause of lipoid CAH.

Figure 12:
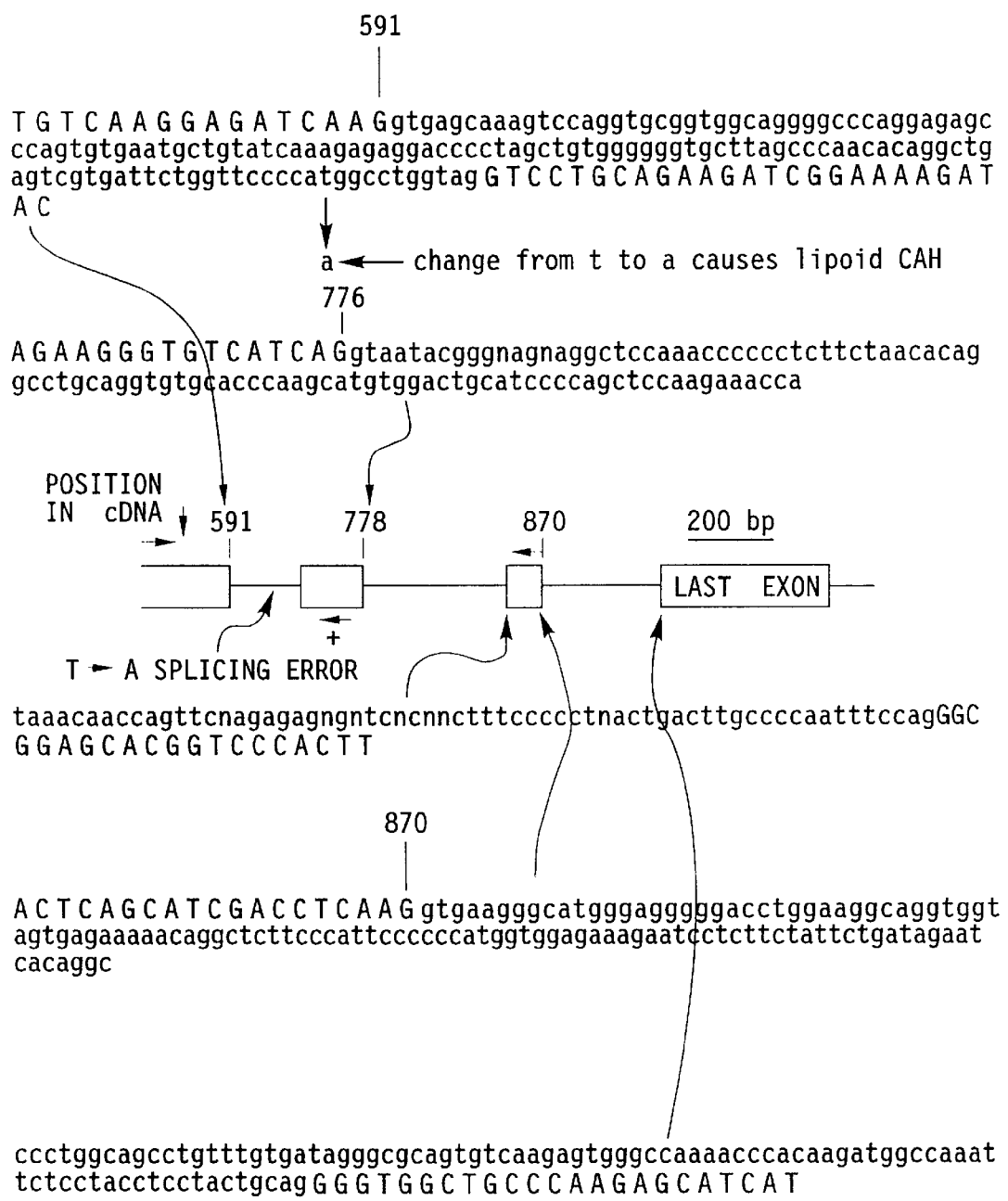
FIG. 12. Splice map for production of human StAR pseudogene. This Figure shows the sequences of all of one intron (SEQ ID NO:14) and parts of two others (SEQ ID NO:15–18) of the StAR gene. These sequences were determined from the 2.1 kb genomic PCR fragment obtained with primers S3 and AS1 in conjunction with the sequence obtained from S2 and AS2, as shown in FIG. 2 above. A change of T to A eleven bases from the splice junction shown will cause lipoid CAH. The inventors found a patient homozygous for this mutation and found that the mutation causes a splicing error that then deletes the following exon. This has been established both in genomic DNA (T to A mutation) and cDNA (deleted exon). Furthermore, the deletion, which is in-frame, results in a non-functional protein, as shown by transfection of an expression vector.

Molecules containing the full-length StAR cDNA sequence (SEQ ID NO:1) are useful as sources of subsequences (discussed below) or as starting materials for the preparation of the StAR molecule itself. A "subsequence" is a group of consecutive nucleotides from one of the indicated full-length sequences (SEQ ID NOS:1, 3 and 4). Such subsequences can be prepared by chemical synthesis from starting nucleotides (as in an automated gene synthesizer) or by biochemical manipulation of the full-length sequences (SEQ ID NOS:1, 3 and 4)(e.g., using restriction endonucleases to prepare fragments, optionally followed by (1) cleavage of terminal nucleotides with exonucleases and/or (2) size sorting and/or affinity capture to select the desired sequence). Any subsequence of the StAR cDNA sequence (SEQ ID NO:1) of sufficient length to be unique under the conditions being used is useful as one of the two primers used in a polymerase chain reaction (PCR) amplification of all or part of the genomic StAR gene as part of a method of identifying the presence or absence of a given StAR gene mutation, such as those described in this specification; the second primer is simply selected from the opposite strand sequence so that the mutation or other sequence to be amplied lies between the two primers. Another preferred subsequence is one that contains a mutation from the normal sequences described herein, as such sequences can be used in allele-specific hybridization techniques to detect the presence of specific mutants. Preferred subsequences also include those that can distinguish between the normal StAR gene and the pseudogene (i.e., that are not found in both the normal StAR gene cDNA of FIGS. 10A-1, 10A-2, and 10B, or the StAR pseudogene of FIGS. 11A and 11B or that span the alternative splice region shown in FIG. 12).

The length of a subsequence necessary to uniquely hybridize with the desired target sequence will vary with the particular method being used and is within the ordinary skill of those who carry out routine identification of genetic material. Typical primers are at least 10, preferably at least 14, more preferably at least 17, even more preferably at least 20 nucleotides in length and typically no more than 200, preferably no more than 100, more preferably no more than 70, even more preferably no more than 50 nucleotides in length. The most preferred subsequences are found in at least one of the human StAR sequences (SEQ ID NOS:1, 3 and 4) set forth in FIGS. 10A-1, 10A-2, 10B, 11A, and 11B but are not found in mouse StAR DNA.

In addition to those molecules that contain sequences and subsequences identical to the those of the StAR gene, molecules containing mutated sequences are also useful, as they can be used as specific probes for mutations. For example, several mutations of amino-acid-encoding codons into stop codons (i.e. nonsense mutations) are identified in the following examples; e.g., $Arg^{193} \rightarrow Stop$ and $Gln^{258} \rightarrow Stop$ mutations. (Here and elsewhere in this specification "codon" refers to a nucleic acid triplet in the reading frame of the gene, unless otherwise clear from the context.) Thus, a preferred class of mutant-sequence molecules are those that contain a replacement (or more than one replacement) of a nucleotide that converts a codon to a stop codon at a location other than the 3' terminus of the coding sequence, so that a truncated, non-functional StAR polypeptide molecule is encoded. The mutated codon is located preferably at least 5, more preferably 10, even more preferably 20, still more preferably 30 codons distant from the 3' terminus of the normal coding sequence so that sufficient deletion would occur in the targent to produce a non-functional product. Other preferred classes of mutant-sequence molecules are those known to produce non-functional StAR molecules, such as those resulting in non-conservative amino acid replacement, and those that alter translation or transcription signal sequences present in the gene or that introduce improper translation or transcription signal sequences.

It will be recognized that the discussion immediately above refers to sequences and subsequences in the sense strand of genomic DNA. Such sequences can be used to detect the presence of the anti-sense strand of genomic DNA as a result of their complementary nature. However, it is also possible to use a sequence complementary to any of those discussed above, since they will be complementary to and detect the sense strand.

Molecules of the invention will contain a sequence that is different from the mouse genomic StAR gene sequence (in the region from the initiation codon to the stop codon for the StAR gene product) and at least 95% identical to the human StAR cDNA or genomic sequence. By 95% identical is meant that the sequence in question contains no more than 5% different nucleotides from the sequence to which it is being compared, counting each insertion, deletion, or substitution of a nucleotide as a single difference. It will be apparant that a sequence less than 20 nucleotides in length will have to be identical to the standard sequence if it is to be greater than 95% identical.

Identity and relative identity can readily be understood by reference to the following examples. For example, if the hypothetical sequence abcdabcdabcdabcdabcdabcdabcdabcdabcdabcd, which is 40 "nucleotides" in length, is considered to be the standard against which a measurement is being made, each of the following hypothetical nucleotide sequences is 95% identical to the standard sequence (i.e., each has two single-nucleotide differences from the standard 40-nucleotide sequence):

abcdabcdabcdabcdabcdabcdabcdabcdabcdab
[two deletions at 3' terminus];
abcabcdabcdabcdabcabcdabcdabcdabcdabcd
[two random-location deletions];
ababcdabcdabcdabcdabcdabcdabcdabcdabcdabcd
[two insertion at 5' terminus];
abcdabcdabcdabdabcdabcdabcdabcdaabcdabcd
[one random insertion and one random deletion];
abcdabcdbbcdabcdabcdabcdabcdabcdbbcdabcd
[replacement of two "a" nucleotides by "b" nucleotides]; and
abcdabcbabcdabcdabcdabcdabcadabcdabcdabcd
[one replacement and one insertion].

It will be apparant that many similar examples could be given, particularly with molecules of the invention, which are often of larger size than these examples. However, these examples should suffice to teach a person of ordinary skill the meaning of "% different" as used herein. It will also be readily recognized that the sequences to be compared will be aligned for maximum identity before differences are calculated; while computer programs (such as the FASTA program, described in Pearson, W. R., and Lipman, D. J., *Proc. Natl. Acad. Sci. USA,* 85 2444–2448 (1988)) can be used, the high degree of required homology means that visual sequence comparisons will readily find the maximum homology alignment.

The specific sequences indicated above to be derived from or otherwise related to a StAR gene can be the entire sequence of a polynucleotide or can be part of a larger sequence. For example, sandwich hybridization assays that utilize long polynucleotide sequences containing subsequences that hybridize with different molecules (such as target genomic sequences or sequences present in a second polynucleotide that acts as an anchor to a solid surface) are well known. See, for example, U.S. Pat. Nos. 5,288,609 and 5,124,246.

The word "isolated," when used to refer to a polynucleotide molecule characterized by the sequences set forth in this specification, means separated from at least some of the genomic DNA normally associated with the StAR gene and preferably separated from all human cellular materials other than polynucleotides. Gene libraries that may have contained a vector containing an unidentified segment of genomic DNA including the StAR gene are not "isolated," as the StAR gene was not known to be present and/or was not separated from vectors containing other human DNA. In most cases, an isolated molecule of the invention will have a length of less than 50 kb, preferably less than 30 kb, more preferably less than 20 kb. Minimum lengths have been previously discussed.

Generally, the compositions of the invention will be used in a method of detecting the presence of a genetic defect that causes or may cause congenital lipoid adrenal hyperplasia in a human or that can or may transmit congenital lipoid adrenal hyperplasia to an offspring of the human, in which the compositions are used to identify a mutation of a StAR gene of the human. Initially, genetic counselors and others will be looking simply for differences from the StAR gene sequence now identified as being normal and not associated with disease, since any deviation from this sequence has the potential of causing disease, which is a sufficient basis for genetic counseling, particularly if the different (but still unconfirmed) gene is found in a person with a family history of congenital lipoid adrenal hyperplasia. As specific mutations are identified as being positively correlated with congenital lipoid adrenal hyperplasia (or its absence), genetic counselors will in some cases focus on identifying one or more specific mutations of the StAR gene that changes the sequence of a protein product of the StAR gene or that results in the StAR gene not being transcribed or translated. However, simple identification of the presence or absence of any mutation in the StAR gene of a patient will continue to be a viable part of genetic analysis and counseling.

The actual technique used to identify the StAR gene or a StAR gene mutant is not itself part of the practice of the invention. Any of the many techniques that can be used to identify gene mutations, whether now known or later developed, can be used, such as hybridization with specific probes, which includes the technique known as allele-specific oligonucleotide hybridization (either without amplification or after amplification of the region being detected, such as by PCR), restriction fragment length polymorphism (RFLP) analysis, or random amplified polymorphic DNA (RAPD) analysis. Other analysis techniques include enzymatic mismatch scanning and transcription/translation analysis. All of these techniques are described in a number of patents and other publications; see, for example, for RFLPs, D. Botstein et al., in the American Journal of Human Genetics 32 314–321 (1980), and for RAPDs, J. G. K. Williams et al., in Nucleic Acids Research 18 6531–6535 (1990).

Depending on the patient being tested, different identification techniques can be selected to achieve particularly advantageous results. For example, for a group of patients belonging to a particular racial or ethnic group known to be associated with a particular mutation of the StAR gene, allele-specific oligonucleotide (ASO) hybridization is a preferred technique. For screening of large, mixed-origin populations, single-strand conformation polymorphism is preferred. For an individual, total sequencing of genetic and/or cDNA and comparison with standard sequences, such as those shown herein (SEQ ID NOS:1, 3 and 4), are preferred.

In many identification techniques, some amplification of the host genomic DNA (or of messenger RNA) will take place to provide for greater sensitivity of analysis. In such cases it is not necessary to amplify the entire StAR gene, merely the part of the gene or the specific location within the gene that is being detected. Thus, the method of the invention generally comprises amplification (such as via PCR) of at least a segment of the StAR gene, with the segment being selected for the particular analysis being conducted by the diagnostician.

Since lipoid CAH is an autosomal recessive genetic disease, the method of the invention in some cases will classify the patient as homozygous for the normal StAR gene or for the mutated StAR gene or heterozygous for the normal StAR gene and the mutated StAR gene, since this information is informative for genetic counseling.

The patient on who diagnosis is being carried out can be an adult, as is usually the case for genetic counseling, or a newborn, or prenatal diagnosis can be carried out on a fetus. Blood samples are usually used for genetic analysis of adults or newborns (e.g., screening of dried blood on filter paper), while samples for prenatal diagnosis are usually obtained by amniocentesis or chorionic villus biopsy.

The full-length normal StAR genes from humans, as well as shorter genes that produce functional StAR proteins, can be used to correct congenital lipoid adrenal hyperplasia in a human patient by supplying to the human an effective amount of a gene product of a human StAR gene, either by gene therapy or by in vitro production of the StAR protein followed by administration of the protein. Since lipoid CAH is recessive and is thus treatable by supplementary supply of StAR, such treatment is readily accessible. It should be recognized that the various techniques for administering genetic materials or gene products are well known and are not themselves part of the invention. The invention merely involves supplying the genetic materials or proteins of the invention in place of the genetic materials or proteins previously administered. For example, techniques for transforming cells to produce gene products are described in U.S. Pat. No. 5,283,185 entitled "Method for Delivering Nucleic Acid into Cells," as well as in numerous scientific articles, such as Felgner et al., "Lipofection: A Highly Efficient, Lipid-Mediated DNA-Transfection Procedure," *Proc. Natl. Acac. Sci. U.S.A.*, 84 7413–7417 (1987); techniques for in vivo protein production are described in, for example, Mueller et al., "Laboratory Methods—Efficient Transfection and Expression of Heterologous Genes in PC12 Cells," *DNA and Cell Biol.*, 9(3), 221–229 (1990). Administration of proteins to overcome a deficiency disease is so well known (e.g., administration of insulin to correct for high blood sugar in diabetes) that further discussion of this technique is not necessary. Some modification of existing techniques may be required for particular applications, but those modifications are within the skill level of the ordinary practioner using existing knowledge and the guidance provided in this specification.

The invention now being generally described, the same will be better understood by reference to the following detailed examples, which are provided for purposes of illustration only and are not to be considered limiting of the invention.

EXAMPLES

Example 1

Isolation of human StAR cDNA clones and DNA sequence analysis

A human adrenal cortex cDNA library in lambda gt22A, prepared from poly (A)+ RNA isolated from the adrenal cortex of an 18 year old male, was provided by Drs. Andre Lacroix, Alain Belanger, and Yves Tremblay, University of Laval, Quebec, Canada. The library was screened with a partial-length mouse StAR cDNA (Clark et al., 1994). More than 50 positive clones were detected in the screening of 600,000 plaques. Two plaque-purified phage clones were selected for sequence analysis. Each contained an insert of approximately 1.6 kb. Both inserts were subcloned into pSPORT (GIBO-BRL, Bethesda, Md.) and sequenced utilizing an automated DNA sequencer (Applied Biosystems, Inc.) employing Taq dideoxy sequencing reagents. Ambiguities were corrected by manual sequencing.

The two human StAR cDNAs that were characterized by DNA sequence analysis had identical 126 nt 5'-untranslated regions. Both clones contained an 855 nt open reading frame encoding a 285 amino acid protein. The 1.6 kb cDNA whose nucleotide sequence is shown in FIG. 4 (SEQ ID NO:1) had a 623 nt 3'-untranslated sequence that ended in a poly (A)+ tail preceded 23 nt upstream by an AATAAA sequence.

The deduced human StAR amino acid sequence (SEQ ID NO:2) is 84% identical to that of mouse StAR (Clark et al., 1994) (FIGS. 4-1 and 4-2). It contains a 25 amino acid N-terminal sequence that is comprised of basic and hydrophobic amino acids that are characteristic of mitochondrial targeting sequences. Seven consensus sites for phosphorylation by cAMP-dependent protein kinase and three protein kinase C phosphorylation sites are present in the sequence of the mature protein. Expression of StAR in engineered COS-1 cells increases steroidogenesis Example 2

Expression of StAR cDNA in COS-1 cells

To examine the functional activity of the human StAR protein, we utilized methods that we previously employed to explore the function of sterol carrier protein 2 in steroidogenesis (Yamamoto, R., Kallen, C. B., Babalola, G. O., Rennert, H., Billheimer, J. T., Strauss, III J. F. (1991) Proc. Natl. Acad. Sci. USA 88: 463–467). Briefly, COS-1 cells were transfected with various expression vectors with Lipofectamine (GIBCO-BRL) using 10 µl/dish. The vectors included pSPORT without cDNA insert, pSPORT with the 1.6 kb StAR cDNA (pStAR), and expression vectors for bovine P450scc (pCDP450scc) and adrenodoxin (pCDADX), provided by Dr. Michael Waterman, Vanderbilt University (Nashville, Tenn.). Forty-eight hours after transfection, medium was collected for radioimmunoassay of pregnenolone as previously described (Yamamoto, R., Kallen, C. B., Babalola, G. O., Rennert, H., Billheimer, J. T., Strauss, III J. F. (1991) Proc. Natl. Acad. Sci. USA 88: 463–467). In one experiment, the hydroxysterol, 20α-hydroxycholesterol, was added (5 µg/ml) to the incubation medium. This hydroxysterol is a more soluble pregnenolone precursor and an intermediate in the cholesterol side-chain cleavage reaction. Hydroxysterols, like 20α-hydroxycholesterol, by-pass the regulated translocation mechanism of cholesterol movement and, therefore, generally provide an index of maximal cholesterol side-chain cleavage activity (Toaff, M. E., Scleyer H., Strauss, J. F., III (1982) Endocrinology 1785–1790). Preliminary studies established that the transfected COS cells secreted about 10-fold more pregnenolone than progesterone and that the measured progesterone levels changed in parallel with the pregnenolone. Consequently, we monitored pregnenolone secretion as our index of steroidogenic response.

COS-1 cells did not secrete pregnenolone when transfected with the pSPORT vector lacking a cDNA insert or the pSPORT vector harboring the StAR cDNA (Table 2). However, co-tranfection of the cells with plasmids directing expression of bovine P450scc and adrenodoxin endowed the cells with steroidogenic activity. Triple transfection of the COS-1 cells with P450scc, adrenodoxin and StAR expression plasmids consistently increased steroid secretion 4-to-20-fold over cells transfected with P450scc, adrenodoxin and the control pSPORT plasmid. Incubation of cells transfected with pP450scc, pADX and pSPORT with 20α-hydroxycholesterol, a relatively soluble intermediate of the cholesterol side-chain cleavage reaction, stimulated pregnenolone secretion to the same extent as pStAR but did not augment the pStAR response in COS cells co-transfected with P450scc and adrenodoxin plasmids. In the absence of P450scc and adrenodoxin expression, there was no detectable pregnenolone synthesis in the presence of 20α-hydroxycholesterol. These findings document that the pSPORT plasmid "control" did not interfere with expression of the steroidogenic enzymes. The fact that an exogenous hydroxycholesterol did not augment steroid production stimulated by StAR also suggests that StAR promotes nearly maximal steroidogenic activity in the transfected COS cells.

The more than 4-fold increase in steroidogenesis promoted by expression of StAR in the COS cell system is substantially greater than the 2-fold increase we observed when COS cells were transfected with sterol carrier protein 2 expression plasmids as the vehicle for enhancement of steroidogenesis (Yamamoto, R., Kallen, C. B., Babalola, G. O., Rennert, H., Billheimer, J. T., Strauss, III J. F. (1991) Proc. Natl. Acad. Sci. USA 88: 463–467). While these observations are consonant with the idea that StAR facilitates steroidogenesis, these studies do not define the exact mechanism of StAR action.

TABLE 2

Stimulation of steroidogenesis by StAR in COS-1 cells transfected with cholesterol side-chain cleavage enzyme and adrenodoxin.

| Treatment | Pregnenolone secretion (ng/dish) | | | |
| --- | --- | --- | --- | --- |
| | Expt. 1 | Expt. 2 | Expt. 3 | Expt. 4 |
| Mock transfection | <5 | | | |
| pSPORT | <5 | | | |
| pStAR | <5 | | | |
| pStAR + 20α-OH—C | | | | <5 |
| pCDP450scc + pCDADX + pSPORT | 26 ± 6 | 14 ± 1.0 | 10 ± 0.01 | 20 ± 0.5 |
| pCDP450scc + pCDADX + pSPORT + 20α-OH—C | | | | 157 ± 10 |
| pCDP450scc + pCDADX + pStAR | 545 ± 50 | 78 ± 4 | 41 ± 2.0 | 175 ± 10 |
| pCDP450scc + pCDADX + pStAR + 20α-OH—C | | | | 137 ± 8 |

COS-1 cells were transfected with the indicated plasmids (2 µg plasmid/35 mm dish) with Lipofectamine. The media were collected after 48 h and assayed for pregnenolone by radioimmunoassay. 20α-hydroxycholesterol (20α-OH—C; 5 µg/ml) was added to some cultures. The results of 4 separate experiments are presented. Values are means ± S.E., N = 3–4 replicates per experiment.

Example 3

Expression of StAR mRNA

Northern blots containing 2 µg of poly (A)+ RNA from various human tissues were purchased from Clontech Laboratories (Palo Alto, Calif.) and probed with the 1.6 kb StAR cDNA and a β-actin cDNA according to the supplier's protocol.

Figure 5:
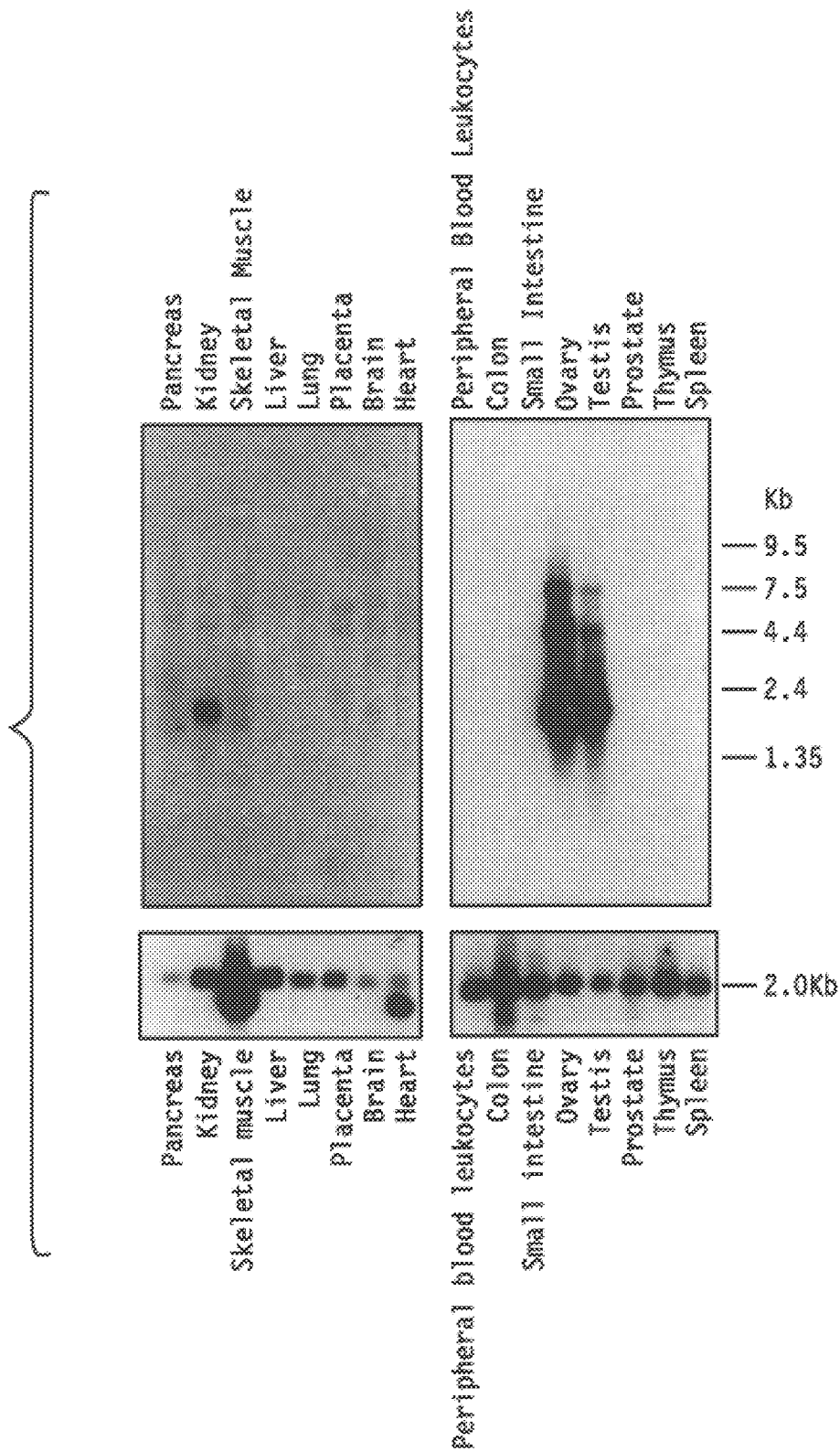
FIG. 5. Expression of StAR mRNA in various human tissues. Northern blots containing 2 $\mu$g of poly (A)+ RNA isolated from the indicated tissues were purchased from Clontech Laboratories and probed sequentially with StAR and $\beta$-actin cDNAs. The autoradiogram in the left hand panel A for StAR was exposed for 24 h, the right hand panel A autoradiogram for StAR was exposed for 4 h. The blots were both exposed for 2 h for actin (B).

StAR mRNA was detected in human ovary, testis and kidney. The most abundant transcript was 1.6 kb and less abundant mRNAs of 4.4 and 7.5 kb were observed in ovary and testis (FIG. 5). The ovarian sample, prepared from a pool of five ovaries obtained from women of reproductive age, contained the most StAR mRNA followed by the testis and then the kidney. In the Northern blots shown in FIG. 5, probed simultaneously with the same preparation of $^{32}$P- labeled cDNAs, the blot containing the ovary and testis was exposed for 6 h for expression of StAR whereas the blot containing the kidney sample was exposed for 24 h for StAR. Longer exposures of both blots failed to reveal StAR mRNA in placenta, pancreas, skeletal muscle, liver, lung, brain, heart, peripheral blood leukocytes, colon, small intestine, prostate, thymus and spleen. However, β-actin mRNA was readily detected in all of these tissues on the same blots. StAR expression in human adrenal cortex is inferred from the fact that multiple StAR phage clones were detected in the library used to isolate the human StAR cDNA.

These observations suggest that StAR expression is restricted to organs that carry out mitochondrial sterol hydroxylation reactions that are under acute regulation by tropic hormones that act via the intermediacy of cAMP. This is true for the adrenals and gonads, which respond to their respective pituitary tropic hormones, ACTH and LH, with enhanced cholesterol side-chain cleavage, and to the kidney, which increases 1α-hydroxylation of vitamin D in response to PTH. It is notable that another steroidogenic organ, the placenta, does not appear to express StAR. However, placental progesterone does not seem to be under acute regulation by cAMP. The reported stimulatory effect of agents that raise placental trophoblast cAMP levels or cAMP analogs is most likely related to increased expression of genes encoding steroidogenic enzymes, a process that takes hours or days (Golos, T. G., Miller, W. L., Strauss, III, J. F. (1987) J. Clin. Invest. 80: 896–899). The brain, which is also a site of steroidogenesis (Patterson, D., Jones, C., Hart, I., Bleskan, J., Berger, R., Geyer, D., Eisenberg, S. P., Smith, M. F., Jr., Arend, W. P. (1993) Genomics 15: 173–176), did not appear to express StAR either. The absence of StAR expression in the placenta and brain suggests that steroid hormone synthesis in these organs is regulated by other mechanisms, a suggestion that has been previously made by Lieberman and colleagues (Lieberman, S., Prasad, V. V. K. (1990) Endocr. Rev. 11: 469–493).

Total RNA was also isolated from cultures of human granulosa cells obtained from women undergoing in vitro fertilization/embryo transfer, or from purified human cytotrophoblast cells. The human granulosa cells were cultured for 4 days and then treated with 1.5 mM 8-bromo-cAMP for 24 h. The cytotrophoblast cells were cultured for 24 h in the absence or presence of 1.5 mM 8-bromo-cAMP. Detailed protocols for the preparation, culture and isolation of total RNA from the granulosa cells and trophoblast cells have been described previously (Golos, T. G., Miller, W. L., Strauss, III, J. F. (1987) J. Clin. Invest. 80: 896–899; Ringler, G. E., Kao, L.-C., Miller, W. L., Strauss, III, J. F. (1989) Mol. Cell. Endocrinol. 61: 13–21). Northern blots were probed with the StAR cDNA and a cDNA encoding human 28 S rRNA.

Figure 6:
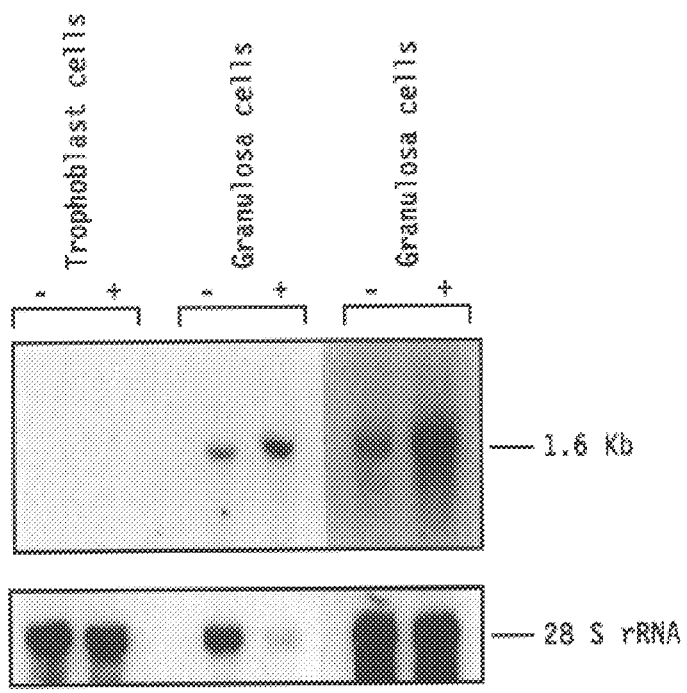
FIG. 6. Regulation of StAR mRNA expression in human granulosa cells by cAMP. Primary cultures of human granulosa cells were established in culture for 4 days and then 8-bromo-cAMP (1.5 mM) was added to some dishes (+) for a 24 h period. Results from two separate experiments are presented. Primary cultures of human trophoblast cells were also established in the absence (−) or presence (+) of 1.5 mM 8-bromo-cAMP for 24 h. Total RNA was extracted and subjected to Northern blotting (5 $\mu$g RNA/lane) and the blots were probed sequentially with StAR and 28 S rRNA cDNA probes. Autoradiograms were analyzed with an image analysis system (Resource Technology, Nashville, Tenn.) to determine the increase in StAR mRNA in the human granulosa cells relative to 28 S rRNA. The increase was 3-fold in one experiment and 7-fold in the other.

Culture of human granulosa cells in the presence of 1.5 mM 8-bromo-cAMP for 24 h increased StAR mRNA 3-to 7-fold relative to 28 S rRNA (FIG. 6). In contrast, StAR mRNA was not detectable in primary cultures of human trophoblast cells incubated for 24 h without or with the cyclic AMP analog. StAR mRNA was also not detected in Northern blots of poly (A)+ RNA isolated from JEG-3 choriocarcinoma cells cultured for 24 h without or with 8-bromo-cAMP (data not shown), a treatment that up-regulates P450scc and adrenodoxin gene expression (Picado-Leonard, J., Voutilainen, R., Kao, L.-C., Chung, B.-C., Strauss, III, J. F., Miller, W. L. (1988) J. Biol. Chem. 263: 3240–3244). These observations suggest that tropic hormones may control levels of StAR in part by increasing the mRNA encoding the protein and hence its synthesis.

Example 4
Mapping of the StAR structural gene and pseudogene

The StAR gene and its pseudogene were mapped by hybridization to Southern blots of DNA from somatic cell hybrids and by polymerase chain reaction analyses using primers specific for the structural gene or pseudogene. High molecular weight genomic DNAs from human x hamster and human x mouse somatic cell hybrid lines obtained from the NIGMS Human Genetic Mutant Cell Repository (1992/1993 Catalog of Cell Lines, National Institutes of Health) and DNA from human x hamster somatic cell hybrids purchased from BIOS Corporation (New Haven, Conn.) were used to assign the chromosomal localization of the structural gene and pseudogene.

Regional mapping of the StAR structural gene was accomplished with a chromosome 8 regional mapping panel consisting of hybrids 9HL10, ISHL27 and 20XP0435-2, supplied by Dr. M. Wagner (Chang, Y. J., McCabe, R. T., Rennert, H., Budarf, M. L., Sayegh. R., Emanuel, B. S., Skolnick, P., Strauss, III, J. F. (1992) DNA Cell Biol. 11: 471–480), 8q–, 21q+ and C117 (Wagner, M. J., Ge, Y., Siciliano, M., Wells, D. E. (1991) Genomics 10: 114–125; Dalla-Favera, R., Bregni, M., Erikson, J., Patterson, D., Gallo, R. C., Croce, C. M. (1982) Proc. Natl. Acad. Sci. U.S.A. 82: 464–468; Drabkin, H. A., Diaz, M., Bradley. C. M., Le Beau, MM., Rowley, J. D., Patterson, D. (1985) Proc. Natl. Acad. Sci. U.S.A. 82: 464–468.), and Rec8, which is a hybrid produced by the fusion of the GlyB CHO-K1 mutant with cells from a patient suffering from Recombinant 8 Syndrome (Sacchi, N., Cheng, S. V., Tanzi, R. E., Gusella, J. F., Drabkin, H. A., Patterson, D., Haines, J. H., Papas, T. S. (1988) Genomics 3: 110–116). This cell line contains the Recombinant 8 chromosome, but has no normal human chromosome 8.

Figure 7:
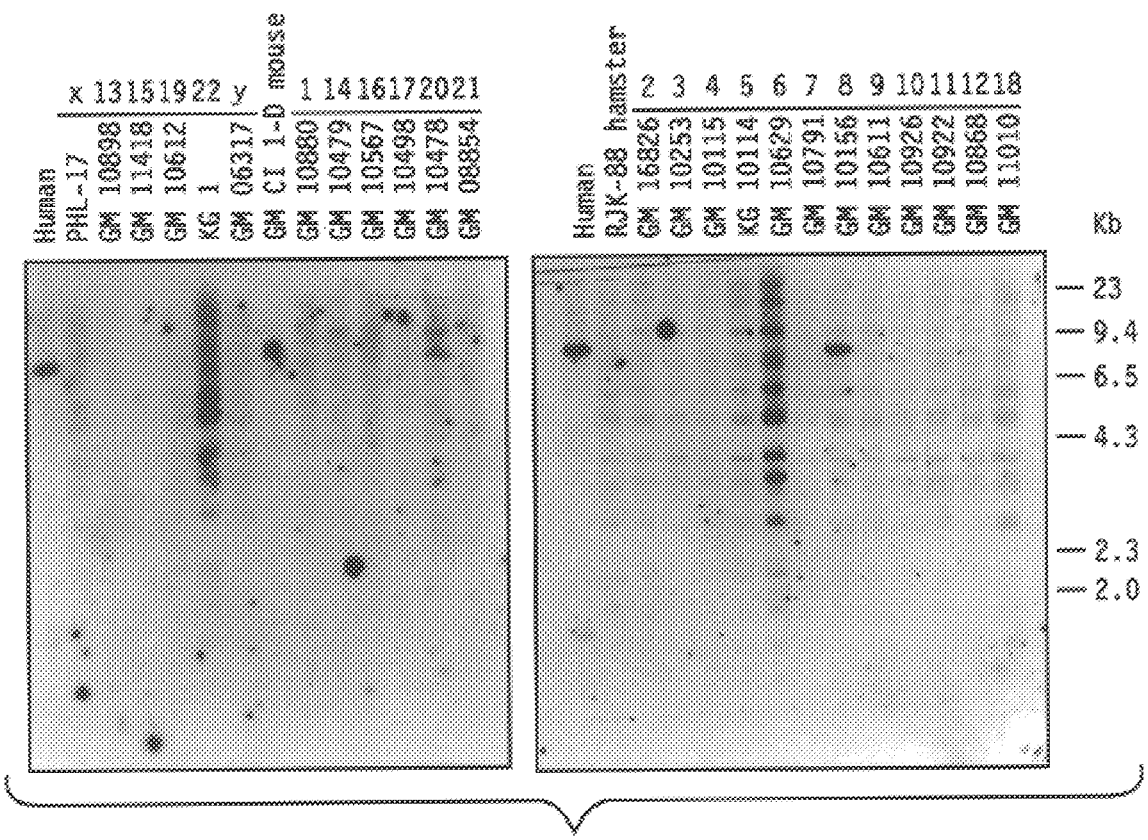
FIG. 7. Assignment of the StAR gene to human chromosome 8. Genomic DNA was isolated from a panel of somatic cell hybrids, digested with Hind III and subjected to Southern blotting. The hybrid designation and the human chromosome that predominates, which in some cases is the only human chromosome present in the hybrid, are indicated. A hybridization band corresponding to that found in human genomic DNA was found in a hybrid containing only human chromosome 8. A weaker band was found in hybrid GM 10478, which in addition to chromosome 20 is known to contain a fragment of 8p.

When genomic DNA from the hybrid panel was digested with Hind III and subjected to Southern blotting (technical details of Southern blotting are set out below), a strong hybridization band of about 8 kb was detected in the human genomic DNA control and in hybrid GM 10156, which contains only human chromosome 8 (FIG. 7). A faint band was also detected in GM 10478, which in addition to containing human chromosome 20 also contains a fragment of human chromosome 8p. These findings indicated that file StAR gene resides on chromosome 8.

To confirm the localization of the StAR gene to chromosome 8, we examined somatic cell hybrid DNA by PCR with primers that specifically amplify the structural gene. Hybrids containing chromosome 8 gave a positive signal whereas all other hybrids, including those known to contain human chromosome 20 but not 8, did not yield a specific amplification product (data not shown).

Figure 8A:
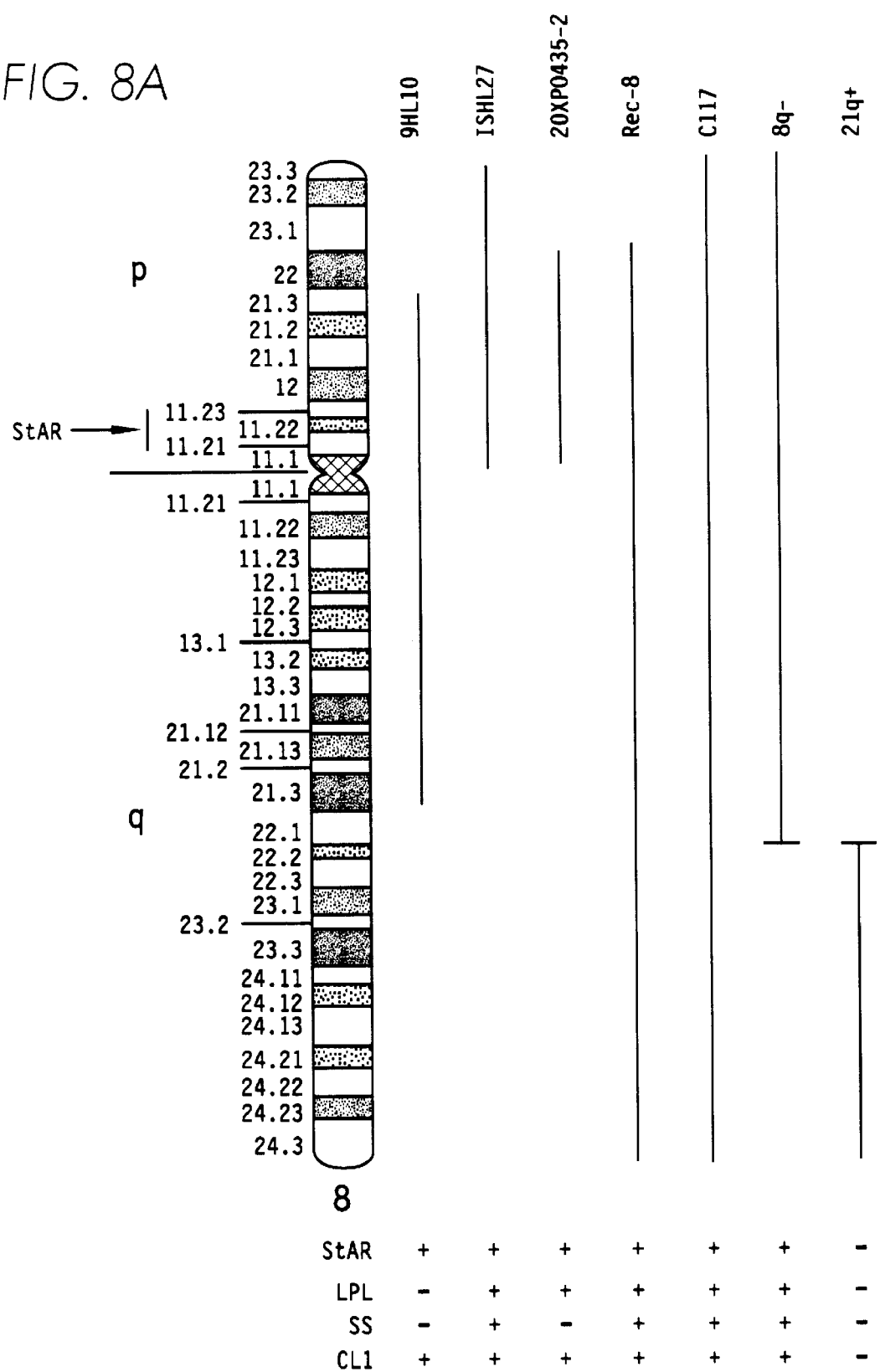

Analysis of a human chromosome 8 regional mapping panel placed the StAR gene on 8p (FIG. 8A). Confirmation and refinement of the regional mapping of the functional StAR gene was carried out by isolating a YAC containing the StAR functional gene and using this YAC as a probe in FISH (FIG. 8B). Regional mapping was done by sequential banding followed by FISH. By this method the StAR locus was assigned to 8p11.2. Simultaneous FISH with the StAR YAC and an 8 centromere-specific probe as well as fractional length measurements confirmed this assignment.

PCR analysis of reverse transcribed RNA from human testis and PCR analysis of human genomic DNA suggested the existence of an expressed StAR pseudogene. DNA sequences of the amplified pseudogene product did not contain introns and differed in a large number of positions from the functional StAR gene sequence in terms of nucleotide insertions, deletions and substitutions. The amplified sequences differed among several individuals, suggesting significant polymorphism. Using primers specific for the pseudogene sequences, we determined that a StAR pseudogene resides on chromosomes 13 (FIG. 9).

Example 5
Southern blotting and PCR Analysis

Ten-12 μg of genomic DNA from each of 24 somatic cell hybrids, total human, hamster (RJK88) and mouse (GM C1 1-D) were digested with Hind III and electrophoresed through 0.8% agarose and blotted to Hybond N+ (Amersham, Aylesbury, United Kingdom) membranes. Hybridizations with StAR cDNA were performed using previously described conditions (Chang, Y. J., McCabe, R. T., Rennert, H., Budarf, M. L., Sayegh. R., Emanuel, B. S., Skolnick, P., Strauss, III, J. F. (1992) DNA Cell Biol. 11: 471–480).

The StAR structural gene and pseudogene were mapped by PCR analysis of somatic cell hybrid DNA with sequence specific primers. For the structural gene the forward primer used was 5'-GTGAGCAAAGTCCAGGTGCG-3'(SEQ ID NO:9) and the reverse primer was 5'-TGTGGCCATGCCAGCCAGCA-3'(SEQ ID NO:8). These sequences span a small intron and yield a product of 300 nt. Primers derived from the DNA sequence of the PCR amplified expressed pseudogene, the sequence of which will be reported elsewhere, were used to determine the pseudogene location. The forward primer was 5'-AGCCTCACCGGCGTTGGCGG-3'(SEQ ID NO:19) and the reverse primer was 5'-CTGCAAGACCTTGATCGCCTTG-3'(SEQ ID NO:20). These primers yield a 800 nt pseudogene-specific product. The PCR conditions were denaturation at 94° C. for 5 min followed by a cycle of denaturation at 94° C. for 45 sec, annealing at 65° C. for 45 sec and extension at 72° C. for 2 min for 30 cycles with 10 pM of the primers in a buffer containing 2 mM MgCl$_2$. The PCR products were analyzed by electrophoresis in 1% agarose gels, stained with ethidium bromide.

To confirm the regional mapping of the structural StAR gene, we analyzed the regional mapping panel for several genes known to map to chromosome 8p including the clustrin gene (CL1) (Smith, A. C. M., Spuhler, K., Wiliams, T. M., McConnell, T., Sujansky, E., Robinson, A. (1987) Am. J. Human. Genetics 41: 1083–1103; de Silva, H. V., Harmony, J. A., Stuart, W. D., Gil, C. M., Ribbins, J. (1990) Biochemistry 29: 5380–5389; Jenne, D. E., Tschopp, J. (1989) Proc. Natl. Acad. Sci. U.S.A. 86: 7123–7127; Kirszbaum, L., Sharpe, J. A., Murphy, J., d'Apice, A. J., Classon, B., Hudson, P., Walker, I. D. (1989) EMBO J. 8: 711–718); the lipoprotein lipase gene (LPL) (Pineault, J. M., Tenniswood, M. (1993) J. Biol. Chem. 268: 5021–5031); and the squalene synthase gene (SS) (Wion, K. L., Kirchgessner, T. G., Lusis, A. J., Schotz, M.c., Lawn, R. M. (1987) Science 235: 1638–1641). PCR primers were designed from the published sequences. The CL1-specific primers were 5'-AGAAAGCGCTGCAGGAATACC-3' (SEQ ID NO:21) and 5'-GTGACGTGCAGAGCTCTC-3' (SEQ ID NO:22), representing nt 2504–2524 and 2836–2854, respectively. The LPL-specific primers were 5'GAAACTGGGCGAATCTAC-3'(SEQ ID NO:23) and 5'TTGAAACACCCCAAACACTG-3'(SEQ ID NO:24), representing nt 1601–1620 and 1687–1706, respectively. The SS-specific primers were 5'-AAAAGAACGCTGTGTGGCTGGGAC-3'(SEQ ID NO:25) and 5'-ACCTAAACCGTGGCAAAT-3'(SEQ ID NO:26), representing nt 1405–1428 and 1547–1568, respectively.

Example 6
Fluorescence in situ hybridization (FISH) mapping

An individual yeast artificial chromosome (YAC) colony containing the StAR structural gene was isolated from the St. Louis library by PCR screening using StAR-specific primers corresponding to the 3'-untranslated sequences. The sense primer was 5'-CCTACTGGAAGCCTGCAAGTCTAAG-3'(SEQ ID NO:27)(nt 1048–1072). The antisense primer was 5'-TGGTTTTAGGTGGGTACATAAGGG-3'(SEQ ID NO:28)(nt 1287–1264). StAR sequences in YAC DNA were amplified in a standard PCR reaction vol of 10 μl containing 1 mM MgCl$_2$. YAC DNA was initially denatured at 94° C. for 5 min. Amplification was carried out with 35 cycles of denaturation at 94° C. for 30 sec, annealing at 55° C. for 30 sec and extension at 72° C. for 30 sec. The reaction products were analyzed for the presence of the expected 240 nt amplification product in 2% agarose gels followed by ethidium bromide staining.

YAC FISH was performed as previously described (Jiang, G., McKenzie, T. L., Conrad, D. G., Schechter, I. (1993) J. Biol. Chem. 268: 12818–12824; Lichter, P., Tang, C.-J. C., Call, K., Hermanson, G., Glen, A. E., Housman, D., Ward, D. C. (1990) Science 247: 64–69) with the following modifications: The biotin-labeled probe was denatured at 75° C. for 5 min, pre-annealed with human Cot-1 DNA for 1 h at 37° C. and applied to human chromosome slide preparations that had been previously denatured and dehydrated. Slides were cover-slipped and hybridized overnight in a humid chamber at 37° C. In some experiments, a chromosome 8 centromere-specific probe (D8Z2; Oncor, Inc., Gaithersburg, Md.) was added to the hybridization mixture. Post-hybridization washes were done in 50% formamide/2× SSC (1×SSC=0.15M NaCl and 0.015M sodium citrate) for 15 min and 2×SSC for 8 min. at 45° C. Detection was by avidin-FITC, with one amplification by the manufacturer's directions (Oncor, Inc.). Chromosomes were counter-stained with propidium iodide.

Twelve metaphase spreads were G-banded by trypsin and photographed prior to FISH. Slides were washed in Heme-De (Fisher Scientific, Fairlawn, N.J.) to remove the oil, destained in absolute methanol two times for 10 min, dehydrated in 70% and then 80% ethanol for 2 min each, placed in absolute methanol for 10 min and air dried. FISH was then performed as described above. Metaphase spreads were relocated and banding patterns compared with probe signal to assign location of the probe. Fractional length measurements confirmed the assignment (Jiang, G., McKenzie, T. L., Conrad, D. G., Schechter, I. (1993) J. Biol. Chem. 268: 12818–12824).

Metaphase spreads were either photographed with a Zeiss Axiophot microscope with Ektachrome 400 slide film, or processed digitally by computer and printed with a color printer.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

5,807,678

What is claimed is:

1. A method of detecting the presence or absence of a genetic defect that has the potential of causing congenital lipoid adrenal hyperplasia in a human or of transmitting congenital lipoid adrenal hyperplasia to an offspring of said human, which comprises:

obtaining nucleic acid containing at least a portion of a gene encoding a steroidogenesis acute regulatory protein from said human;

analyzing said nucleic acid for the presence or absence of a mutation of said gene, wherein said mutation provides a sequence different from human steroidogenesis acute regulatory protein genomic DNA sequence as set forth in FIG. 10, whereby presence of said mutation is indicative of a genetic defect having a potential of causing congenital lipoid adrenal hyperplasia.

2. The method of claim 1, wherein said mutation results in a change in the sequence of a protein product of said steroidogenesis acute regulatory protein gene.

3. The method of claim 1, wherein said mutation results in said steroidogenesis acute regulatory protein gene not being transcribed or translated.

4. The method of claim 1, wherein said mutation creates a stop codon in said steroidogenesis acute regulatory protein gene.

5. The method of claim 4, wherein said mutation is an $Arg^{193} \rightarrow Stop$ mutation or a $Gln^{258} \rightarrow Stop$ mutation.

6. The method of claim 1, wherein said method comprises PCR amplification of at least a segment of said steroidogenesis acute regulatory protein gene.

7. The method of claim 1, wherein said method comprises identifying a change in a restriction site as a result of said mutation.

8. The method of claim 1, wherein said method comprises restriction fragment length polymorphism analysis, allele-specific oligonucleotide hybridization, or nucleotide sequencing.

9. The method of claim 1, wherein said method classifies said human as homozygous for said steroidogenesis acute regulatory protein gene or for said mutated steroidogenesis acute regulatory protein gene or heterozygous for said steroidogenesis acute regulatory protein gene and said mutated steroidogenesis acute regulatory protein gene.

* * * * *

UNITED STATES PATENT AND TRADEMARK OFFICE
CERTIFICATE OF CORRECTION

PATENT NO. : 5,807,678
DATED : September 15, 1998
INVENTOR(S) : Walter L. Miller, et al It is certified that error appears in the above-indentified patent and that said Letters Patent is hereby corrected as shown below:

On the title page, item [73], insert -- and Trustees of the University of Pennsylvania, Philadelphia, PA. -- after "Oakland, Calif."

Signed and Sealed this

Ninth Day of November, 1999

*Attest:*

Q. TODD DICKINSON

*Attesting Officer*  Acting Commissioner of Patents and Trademarks

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 1618 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 127..984

( x i ) SEQUENCE DESCRIPTION: SEQ ID NO:1:

```
CCACGCGTCC  GCGAAGCTTG  AGGGGCTCAG  GAAGGACGAA  GCAACCACCC  TTGAGAGAAG        60

AGGCAGCAGC  AGCGGCGGCA  GCAGCAGCGG  CAGCGACCCC  ACCACTGCCA  CATTTGCCAG       120

GAAACA ATG CTG CTA GCG ACA TTC AAG CTG TGC GCT GGG AGC TCC TAC              168
       Met Leu Leu Ala Thr Phe Lys Leu Cys Ala Gly Ser Ser Tyr
        1               5                  10

AGA CAC ATG CGC AAC ATG AAG GGG CTG AGG CAA CAG GCT GTG ATG GCC             216
Arg His Met Arg Asn Met Lys Gly Leu Arg Gln Gln Ala Val Met Ala
 15              20                  25                  30

ATC AGC CAG GAG CTG AAC CGG AGG GCC CTG GGG GGC CCC ACC CCT AGC             264
Ile Ser Gln Glu Leu Asn Arg Arg Ala Leu Gly Gly Pro Thr Pro Ser
                 35                  40                  45

ACG TGG ATT AAC CAG GTT CGG CGG CGG AGC TCT CTA CTC GGT TCT CGG             312
Thr Trp Ile Asn Gln Val Arg Arg Arg Ser Ser Leu Leu Gly Ser Arg
                 50                  55                  60

CTG GAA GAG ACT CTC TAC AGT GAC CAG GAG CTG GCC TAT CTC CAG CAG             360
Leu Glu Glu Thr Leu Tyr Ser Asp Gln Glu Leu Ala Tyr Leu Gln Gln
             65                  70                  75

GGG GAG GAG GCC ATG CAG AAG GCC TTG GGC ATC CTT AGC AAC CAA GAG             408
Gly Glu Glu Ala Met Gln Lys Ala Leu Gly Ile Leu Ser Asn Gln Glu
         80                  85                  90

GGC TGG AAG AAG GAG AGT CAG CAG GAC AAT GGG GAC AAA GTG ATG AGT             456
Gly Trp Lys Lys Glu Ser Gln Gln Asp Asn Gly Asp Lys Val Met Ser
 95              100                 105                 110

AAA GTG GTC CCA GAT GTG GGC AAG GTG TTC CGG CTG GAG GTG GTG GTG             504
Lys Val Val Pro Asp Val Gly Lys Val Phe Arg Leu Glu Val Val Val
                 115                 120                 125

GAC CAG CCC ATG GAG AGG CTC TAT GAA GAG CTC GTG GAG CGC ATG GAA             552
Asp Gln Pro Met Glu Arg Leu Tyr Glu Glu Leu Val Glu Arg Met Glu
                 130                 135                 140

GCA ATG GGG GAG TGG AAC CCC AAT GTC AAG GAG ATC AAG GTC CTG CAG             600
Ala Met Gly Glu Trp Asn Pro Asn Val Lys Glu Ile Lys Val Leu Gln
             145                 150                 155

AAG ATC GGA AAA GAT ACA TTC ATT ACT CAC GAG CTG GCT GCC GAG GCA             648
Lys Ile Gly Lys Asp Thr Phe Ile Thr His Glu Leu Ala Ala Glu Ala
         160                 165                 170

GCA GGA AAC CTG GTG GGG CCC CGT GAC TTT GTG AGC GTG CGC TGT GCC             696
Ala Gly Asn Leu Val Gly Pro Arg Asp Phe Val Ser Val Arg Cys Ala
 175                 180                 185                 190
```

-continued

```
AAG CGC CGA GGC TCC ACC TGT GTG CTG GCT GGC ATG GAC ACA GAC TTC      744
Lys Arg Arg Gly Ser Thr Cys Val Leu Ala Gly Met Asp Thr Asp Phe
            195             200                 205

GGG AAC ATG CCT GAG CAG AAG GGT GTC ATC AGG GCG GAG CAC GGT CCC      792
Gly Asn Met Pro Glu Gln Lys Gly Val Ile Arg Ala Glu His Gly Pro
            210                 215             220

ACT TGC ATG GTG CTT CAC CCG TTG GCT GGA AGT CCC TCT AAG ACC AAA      840
Thr Cys Met Val Leu His Pro Leu Ala Gly Ser Pro Ser Lys Thr Lys
        225                 230             235

CTT ACG TGG CTA CTC AGC ATC GAC CTC AAG GGG TGG CTG CCC AAG AGC      888
Leu Thr Trp Leu Leu Ser Ile Asp Leu Lys Gly Trp Leu Pro Lys Ser
        240                 245             250

ATC ATC AAC CAG GTC CTG TCC CAG ACC CAG GTG GAT TTT GCC AAC CAC      936
Ile Ile Asn Gln Val Leu Ser Gln Thr Gln Val Asp Phe Ala Asn His
255                 260             265                 270

CTG CGC AAG CGC CTG GAG TCC CAC CCT GCC TCT GAA
Leu Arg Lys Arg Leu Glu Ser His Pro Ala Ser Glu
            275             280

GCC AGG TGT TGAAGACCAG           991
                                    Ala Arg Cys
                                            285

CCTGCTGTTC  CCAACTGTGC  CCAGCTGCAC  TGGTACACAC  GCTCATCAGG  AGAATCCCTA  1051

CTGGAAGCCT  GCAAGTCTAA  GATCTCCATC  TGGTGACAGT  GGGATGGGTG  GGGTTCGTGT  1111

TTAGAGTATG  ACACTAGGAT  TCAGATTGGT  GAAGTTTTTA  GTACCAAGAA  AACAGGGATG  1171

AGGCTCTTGG  ATTAAAAGGT  AACTTCATTC  ACTGATTAGC  TATGACATGA  GGGTTCAGGC  1231

CCCTAAAATA  ATTGTAAAAC  TTTTTTTCTG  GGCCCTTATG  TACCCACCTA  AAACCATCTT  1291

TAAAATGCTA  GTGGCTGATA  TGGGTGTGGG  GGATGCTAAC  CACAGGGCCT  GAGAAGTCTT  1351

GCTTTATGGG  CTCAAGAATG  CCATGCGCTG  GCAGTACATG  TGCACAAAGC  AGAATCTCAG  1411

AGGGTCTCCT  GCAGCCCTCT  GCTCCTCCCG  GCCGCTGCAC  AGCAACACCA  CAGAACAAGC  1471

AGCACCCCAC  AGTGGGTGCC  TTCCAGAAAT  ATAGTCCAAG  CTTTCTCTGT  GGAAAAAGAC  1531

AAAACTCATT  AGTAGACATG  TTTCCCTATT  GCTTTCATAG  GCACCAGTCA  GAATAAAGAA  1591

TCATAATTCA  CACCAAAAAA  AAAAAAA                                       1618
```

( 2 ) INFORMATION FOR SEQ ID NO:2:

( i ) SEQUENCE CHARACTERISTICS:
       ( A ) LENGTH: 285 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

```
Met Leu Leu Ala Thr Phe Lys Leu Cys Ala Gly Ser Ser Tyr Arg His
 1               5                  10                  15

Met Arg Asn Met Lys Gly Leu Arg Gln Gln Ala Val Met Ala Ile Ser
            20                  25                  30

Gln Glu Leu Asn Arg Arg Ala Leu Gly Gly Pro Thr Pro Ser Thr Trp
        35                  40                  45

Ile Asn Gln Val Arg Arg Arg Ser Ser Leu Leu Gly Ser Arg Leu Glu
    50                  55                  60

Glu Thr Leu Tyr Ser Asp Gln Glu Leu Ala Tyr Leu Gln Gln Gly Glu
65                  70                  75                  80

Glu Ala Met Gln Lys Ala Leu Gly Ile Leu Ser Asn Gln Glu Gly Trp
                85                  90                  95
```

| Lys | Lys | Glu | Ser | Gln | Gln | Asp | Asn | Gly | Asp | Lys | Val | Met | Ser | Lys | Val |
|---|---|---|---|---|---|---|---|---|---|---|---|---|---|---|---|
| | | | 100 | | | | | 105 | | | | | 110 | | |
| Val | Pro | Asp | Val | Gly | Lys | Val | Phe | Arg | Leu | Glu | Val | Val | Asp | Gln | |
| | | 115 | | | | 120 | | | | | 125 | | | | |
| Pro | Met | Glu | Arg | Leu | Tyr | Glu | Leu | Val | Glu | Arg | Met | Glu | Ala | Met | |
| | 130 | | | | | 135 | | | | 140 | | | | | |
| Gly | Glu | Trp | Asn | Pro | Asn | Val | Lys | Glu | Ile | Lys | Val | Leu | Gln | Lys | Ile |
| 145 | | | | | 150 | | | | 155 | | | | | | 160 |
| Gly | Lys | Asp | Thr | Phe | Ile | Thr | His | Glu | Leu | Ala | Ala | Glu | Ala | Ala | Gly |
| | | | | 165 | | | | | 170 | | | | | 175 | |
| Asn | Leu | Val | Gly | Pro | Arg | Asp | Phe | Val | Ser | Val | Arg | Cys | Ala | Lys | Arg |
| | | | 180 | | | | 185 | | | | | 190 | | | |
| Arg | Gly | Ser | Thr | Cys | Val | Leu | Ala | Gly | Met | Asp | Thr | Asp | Phe | Gly | Asn |
| | | 195 | | | | 200 | | | | | 205 | | | | |
| Met | Pro | Glu | Gln | Lys | Gly | Val | Ile | Arg | Ala | Glu | His | Gly | Pro | Thr | Cys |
| | 210 | | | | | 215 | | | | | 220 | | | | |
| Met | Val | Leu | His | Pro | Leu | Ala | Gly | Ser | Pro | Ser | Lys | Thr | Lys | Leu | Thr |
| 225 | | | | | 230 | | | | | 235 | | | | | 240 |
| Trp | Leu | Leu | Ser | Ile | Asp | Leu | Lys | Gly | Trp | Leu | Pro | Lys | Ser | Ile | Ile |
| | | | | 245 | | | | | 250 | | | | | 255 | |
| Asn | Gln | Val | Leu | Ser | Gln | Thr | Gln | Val | Asp | Phe | Ala | Asn | His | Leu | Arg |
| | | | 260 | | | | | 265 | | | | | 270 | | |
| Lys | Arg | Leu | Glu | Ser | His | Pro | Ala | Ser | Glu | Ala | Arg | Cys | | | |
| | | 275 | | | | | 280 | | | | | 285 | | | |

( 2 ) INFORMATION FOR SEQ ID NO:3:

( i ) SEQUENCE CHARACTERISTICS:
        ( A ) LENGTH: 4016 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: exon
        ( B ) LOCATION: 1098..1283

( i x ) FEATURE:
        ( A ) NAME/KEY: exon
        ( B ) LOCATION: 1620..1733

( i x ) FEATURE:
        ( A ) NAME/KEY: exon
        ( B ) LOCATION: 2047..2174

( i x ) FEATURE:
        ( A ) NAME/KEY: exon
        ( B ) LOCATION: 2267..2425

( i x ) FEATURE:
        ( A ) NAME/KEY: exon
        ( B ) LOCATION: 2567..2751

( i x ) FEATURE:
        ( A ) NAME/KEY: exon
        ( B ) LOCATION: 2828..2921

( i x ) FEATURE:
        ( A ) NAME/KEY: exon
        ( B ) LOCATION: 3031..3765

( i x ) FEATURE:

(A) NAME/KEY: -
(B) LOCATION: 1433..1434
(D) OTHER INFORMATION: /note= "interruption of sequence data"

(ix) FEATURE:
(A) NAME/KEY: -
(B) LOCATION: 2208..2209
(D) OTHER INFORMATION: /note= "interruption of sequence data"

(ix) FEATURE:
(A) NAME/KEY: -
(B) LOCATION: 2781..2782
(D) OTHER INFORMATION: /note= "interruption of sequence data"

(ix) FEATURE:
(A) NAME/KEY: -
(B) LOCATION: 2956..2957
(D) OTHER INFORMATION: /note= "interruption of sequence data"

(xi) SEQUENCE DESCRIPTION: SEQ ID NO:3:

| | | | | | | |
|---|---|---|---|---|---|---|
| GCCCCCCCC | CNACCAGNAC | TCCAAANACC | CAACCTCATG | ANGCTTGGAG | GGGTTCANAA | 60 |
| AAGTGAGAAN | AATTGACAGT | TGAAAACCCA | ACTCCTGGGC | CCCAGGAGGA | CCTNTGAAAG | 120 |
| ATGCTTGAGG | CCAAGAGCTG | GGTTGTTGTA | CTGGCCCTNC | CACTGGCCAG | CTGTTTGACC | 180 |
| CTTGACCAAT | CAAGTNCCAC | TCTGTGGACT | TTCAGGGTCC | TCACCCAGAA | GAAGAGCAGC | 240 |
| CATATGGTCT | CTACTGCCTG | GTAAACACCC | TGGCTCACTC | TCGCGAGATG | GTGGTTCTCA | 300 |
| AAGTGTAGTG | TGTAGTCCAC | ACAACACCTG | CATTGCAACC | ACTGGGTATT | TATTTATTTA | 360 |
| TTTATTTAAT | TTATTTATTT | ATGATGGAGT | CTCACTCTGT | CGCCCAGGAT | GGAGTGCAGT | 420 |
| GGCACGATCT | TGGCTTACTG | CAACCTCTGC | CTCCTGGGTT | CAAGTGATTC | TCATGCCTCA | 480 |
| GCCTCCCGAG | TAGCTGGGAC | TACAGGTGCC | TGCCACATCA | CCCGGCTAAT | TTTTTGTATT | 540 |
| TTTAGTAGAG | ATGAGGNNTC | NCCATGTTGG | CANGCTGGTT | NCGGACGNCT | GACCTCAAGT | 600 |
| GATCTGCCAC | CNCGGCCTNC | CAAAGTGCTG | GGGNTAAAGG | CGTAAACCCA | ACGCCCTGGC | 660 |
| CAAGGGGAGN | TTTTTTCTTT | TCGTTTTNTC | NTNTTTCNTT | TCTTTTCCNT | CNTTNNTTTT | 720 |
| TTNGGTNTTN | NTTTTTTTNN | TAACACAGGT | TTCTGAGCCT | CAATTCCAGA | TCAGCTGAGC | 780 |
| CTGGAGTTTC | TGNAGACAAG | GGCTAGAAAT | CTGCACTTTA | AAGTCTTGAA | AACCNCTGTG | 840 |
| TGCCTTCATC | TAAGCTGCCC | CTGCTTCTCT | CCCCTCCATC | CCTCGCCTGG | CCCTGTCCTC | 900 |
| CCTACTCTCC | CCTGCACCCT | CCCCGCCCC | AAGCTCCCCA | CAAACGGCCA | AAGCAGCAGT | 960 |
| GTGAGGCAAT | CGCTCTATCC | TTGACCCCNT | CCCTTNNACA | GTGAGTGNTG | GCGNTTTTAN | 1020 |
| CTCCTGATGA | TGATGCACAN | CCNTCACCGG | GGGNNAGNTA | AGACGCAGAA | CACCAGGTCC | 1080 |
| AGGCTNCAGC | TGCGGGACTC | AGAGGCGAAG | CTTGAGGGGC | TCAGGAAGGA | CGAAGAACCA | 1140 |
| CCCTTGAGAG | AAGAGGCAGC | AGCAGCGGCG | GCAGCAGCAG | CGGCAGCGAC | CCCACCACTG | 1200 |
| CCACATTTGC | CAGGAAACAA | TGCTGCTAGC | GACATTCAAG | CTGTGCGCTG | GGAGCTCCTA | 1260 |
| CAGACACATG | CGCAACATGA | AGGGTGAGCG | CTGCGGGAAG | GAGGCGATGA | GGGGTTGGCC | 1320 |
| AGCTCTCAGC | GGATGAGGCT | CAGGCCACCC | AATTCTGATC | CTAGTTGTGC | CTCTTACTGG | 1380 |
| GTGAACCTGG | GCAAGTTTCT | TCCCTTCTTG | AATCTCAGTT | TTCCCCTCGG | AAGGGAGCAC | 1440 |
| TACCATGGGA | GNTGAGGTNC | TGGCTCTAGT | TCAGGTCCCT | GCTAGAATAC | TGTGTTNTNN | 1500 |
| TGAGCAAGNC | ACATCCCTCT | CCACNCCCAC | TTACTCATTT | GAGANTANAT | GANGGGGTGG | 1560 |
| NGTGGGCCAT | CTCTAAGGGG | CTTNGCCAGC | TCCTAGACAA | NGGNTATTCC | CTTCTCCAGG | 1620 |
| GCTGAGGCAA | CAGGCTGTGA | TGGCCATCAG | CCAGGAGCTG | AACCGGAGGG | CCCTGGGGGG | 1680 |
| CCCCACCCCT | AGCACGTGGA | TTAACCAGGT | TCGGCGGCGG | AGCTCTCTAC | TCGGTAAGTG | 1740 |
| CTGAGGCTTC | TGGGCTCCTG | GTGCTGCTGG | CAGGAGGTTC | CCTGGAGGGT | GATGTGGTGC | 1800 |

```
ATGTGGCTTT  GGCTCCCCTC  CTGCCATTCC  TTCATTTTGA  GAGGACGTCC  CCAGCCTAGA   1860
GTTCCTCAAG  GCCAGATCCC  TCTCTGGTCA  CCTGGGGCGG  CTGTGATTAA  CTCGACCAGC   1920
AGGCTGGCCC  CTATGGCTTT  AGTCCGGGCT  CTTCAGAGCA  ATGAGCAGAC  CCAGAGCTCC   1980
AGGGATGAGA  GCTGGTGGAG  GCTGGGAGAA  GAAGGAAGCT  CTGTCTCTCC  TCGGATGTGT   2040
ATCCAGGTTC  TCGGCTGGAA  GAGACTCTCT  ACAGTGACCA  GGAGCTGGCC  TATCTCCAGC   2100
AGGGGAGGA   GGCCATGCAG  AAGGCCTTGG  GCATCCTTAG  CAACCAAGAG  GGCTGGAAGA   2160
AGGAGAGTCA  GCAGGTAAGT  GTCGGGGAGA  AGCCTGTGGT  TCCTCCATAT  GCCCGGCCAA   2220
GAATATTTTT  GTCTAACCAC  CTTCTGGGGG  CTCCTTTCTC  TGACAGGACA  ATGGGGACAA   2280
AGTGATGAGT  AAAGTGGTCC  CAGATGTGGG  CAAGGTGTTC  CGGCTGGAGG  TCGTGGTGGA   2340
CCAGCCCATG  GAGAGGCTCT  ATGAAGAGCT  CGTGGAGCGC  ATGGAAGCAA  TGGGGGAGTG   2400
GAACCCCAAT  GTCAAGGAGA  TCAAGGTGAG  CAAAGTCCAG  GTGCGGGTGG  CAGGGGCCCA   2460
GGAGAGCCCA  GTGTGAATGC  TGTATCAAAG  AGAGGACCCC  TAGCTGTGGG  GGGTGCTTAG   2520
CCCAACACAG  GCTGAGTCGT  GATTCTGGTT  CCCCATGGCC  TGGTAGGTCC  TGCAGAAGAT   2580
CGGAAAAGAT  ACATTCATTA  CTCACGAGCT  GGCTGCCGAG  GCAGCAGGAA  ACCTGGTGGG   2640
GCCCCGTGAC  TTTGTGAGCG  TGCGCTGTGC  CAAGCGCCGA  GGCTCCACCT  GTGTGCTGGC   2700
TGGCATGGAC  ACAGACTTCG  GGAACATGCC  TGAGCAGAAG  GGTGTCATCA  GGTAATACGG   2760
GCAGCAGGCT  CCAAACCCCC  CNAGGANTCC  CCACTTTCCN  CCTNACCTNA  CNTTCCCCAA   2820
TTTCCAGGGC  GGAGCACGGT  CCCACTTGCA  TGGTGCTTCA  CCCGTTGGCT  GGAAGTCCCT   2880
CTAAGACCAA  ACTTACGTGG  CTACTCAGCA  TCGACCTCAA  GGTGAAGGGC  ATGGGAGGGG   2940
GACCTGGAAG  GCAGGTTATG  NGANAGGGTG  CAGANTCAAN  CNTGGTGCAT  AGNCCACAAG   3000
ATGAGCACAT  TCTCCTACCA  CCTACTGAAG  GGGTGGCTGC  CAAGAGCAT   CATCAACCAG   3060
GTCCTGTCCC  AGACCCAGGT  GGATTTTGCC  AACCACCTGC  GCAAGCGCCT  GGAGTCCCAC   3120
CCTGCCTCTG  AAGCCAGGTG  TTGAAGACCA  GCCTGCTGTT  CCCAACTGTG  CCCAGCTGCA   3180
CTGGTACACA  CGCTCATCAG  GAGAATCCCT  ACTGGAAGCC  TGCAAGTCTA  AGATCTCCAT   3240
CTGGTGACAG  TGGGATGGGT  GGGGTTCGTG  TTTAGAGTAT  GACACTAGGA  TTCAGATTGG   3300
TGAAGTTTTT  AGTACCAAGA  AAACAGGGAT  GAGGCTCTTG  GATTAAAAGG  TAACTTCATT   3360
CACTGATTAG  CTATGACATG  AGGGTTCAGG  CCCCTAAAAT  AATTGTAAAA  CTTTTTTTCT   3420
GGGCCCTTAT  GTACCCACCT  AAAACCATCT  TTAAATGCT   AGTGGCTGAT  ATGGGTGTGG   3480
GGGATGCTAA  CCACAGGGCC  TGAGAAGTCT  TGCTTTATGG  GCTCAAGAAT  GCCATGCGCT   3540
GGCAGTACAT  GTGCACAAAG  CAGAATCTCA  GAGGGTCTCC  TGCAGCCCTC  TGCTCCTCCC   3600
GGCCGCTGCA  CAGCAACACC  ACAGAACAAG  CAGCACCCCA  CAGTGGGTGC  CTTCCAGAAA   3660
TATAGTCCAA  GCTTTCTCTG  TGGAAAAAGA  CAAAACTCAT  TAGTAGACAT  GTTTCCCTAT   3720
TGCTTTCATA  GGCACCAGTC  AGAATAAAGA  ATCATAATTC  ACACCAAACA  TCAGTCTTTG   3780
TTTTAATATT  GTACTTGTTA  AAAAAATCTA  TGCAGCTGGG  TGCAGTGGCT  CACGCCTGTA   3840
ATCCAGCAT   TTTGGGAGGC  TGAGGTAGGC  GGATCGAGTC  GACTCCCTTT  AGTGAGGGTT   3900
AATTGAGCTC  CACCGCGGTG  GCGGCCGCTC  TAGAACTAGT  GGATCCCCCG  GCTGCAGGA   3960
ATTCGATATC  AAGCTTATCG  ATACCGTCGA  CCTCGAGGGG  GGGCCCGGTA  CCCGGA       4016
```

( 2 ) INFORMATION FOR SEQ ID NO:4:

( i ) SEQUENCE CHARACTERISTICS:
        ( A ) LENGTH: 3487 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

| | | | | | |
|---|---|---|---|---|---|
| GGATCTNTTC | TATAGAAAAC | AAACTCAAGT | GAGGTGGAAA | ATGATGATAT | TCTTCTAATA | 60 |
| AGAGAAAGCT | CAGAAATCAG | AGCTGNGAGA | GTGAAACAGA | AGGAAAGTTA | TGATNTANAG | 120 |
| ACGGGNNGGC | ATGATGTGAT | GAGAAGCGCA | TTTCACTTCT | GTGGCATTGN | CNTCTNAAAC | 180 |
| NTCATNCACT | CCAGTNANNC | ATNNGACNCC | AGNAGACCNN | CCCCACACCT | GAAGGATATT | 240 |
| CTACAAAATG | TTTGATCAGT | ATAATTCAAA | AGTGTCAAGC | TTACAAAAAA | ATAAAGAGTG | 300 |
| AGAACTCATN | NCTGGAGAAC | ACTAGAAAAN | ANTGCAACAT | GGNATCATAG | ATTAAATACT | 360 |
| GAAACAGAAA | AANAGGATAT | TAATGGAAAA | GCTGATAAAN | TCAGAATAAA | GTCTGCAATN | 420 |
| TGATTCACAG | CATCATACGA | NTGTGAATNT | CTAAGTTGTG | ATAAGTGTTT | CATGGNTGNC | 480 |
| TACANTGTNA | ACCTNAGAGA | AACCTGAGTA | AATGGTAAGA | ACTCNCTATA | AAATNNGGCN | 540 |
| ACTATTCTGT | AAATATCNAA | ATAATAATAA | TAAAGAGGAA | ATAGTAGCNA | AACNAATGAA | 600 |
| AACNNGGGAG | TAATACCAAG | AGTGGAAATA | AATTAAAATG | GAACNAGGGG | GACCAAACTA | 660 |
| CATAGACACA | AATTAAANCT | GCAACATNAC | CTAAATATTT | CTTAAAGATA | TTAAGCTTTA | 720 |
| CATATAAAGA | TTATAGAAAT | NCATATCTAC | CTNGATTTTA | ATGACATAAT | GTGTATATTA | 780 |
| AGATTAATCT | GGGTTGTTGN | ACATTTNCTG | TATATTTCTG | AATNGGCACA | TNGCCAGAAT | 840 |
| GAGTAACTGG | CTTGGCATTA | TAATNAACTC | CTGGAGAAAT | NTATTTAGAG | GGAATAAAAC | 900 |
| AATATNTTNG | GCTAAGNCAT | AGAATGGACA | ACTCAGNTAT | GCTTCAGGTN | NTCTTAGTAG | 960 |
| GGAGTATGTG | GGTGNGNGGG | TGGCAGATAA | GCCGCTCACA | TCCTAGGGTT | AGACTTACTG | 1020 |
| GGAAGATCCC | NTGGGATCCG | AAATGGAAGT | CNAAGTTTCT | GTTATCNAAT | TTTNGTGACT | 1080 |
| CCAAAAGGAC | CGGAAAGACC | AGAGATAAGC | ACTAAATGAG | AACNATAAAT | AAGCAAAAG | 1140 |
| GTGTGTCCTA | CCGATTTCAA | TATTCAGTGA | GTCTATAAGA | AGGACCTGAG | CCATCGAGCC | 1200 |
| TGGCCAAAAT | ATTGGATTCT | AATTAAAGAG | TAGAGTGAGG | AGGGGCACAG | AGGACAGCCT | 1260 |
| CCAGGGGGAG | GCCGCACTGC | AAGCATCCCT | GGAGTGGCGA | AGGTATGCAC | TGGATGGATG | 1320 |
| GCAGCAGGCG | CTGCACGGGG | GAGCTGAGCA | CTGCCAGGAA | GAATCCAGTG | AGTGATGGCG | 1380 |
| TTTATCTCTC | CTGATGATGA | TTCACAGCCT | TCAGTGGGGG | ACATTTAATA | CGTGGAACAC | 1440 |
| CGGGTCCAGG | CTGCAGCTGC | GGGACTCAGA | GGCAAAGCTT | GAGTGNCTCA | GGAAGGACGA | 1500 |
| AGAACCACCC | TTGAAAGAAG | AGGCAGCCTC | ACCGGCGTTG | GCGGCCCCAC | CACTGCCACA | 1560 |
| TCTGCCAGGA | AAGATGCTGC | TAGCGACATT | CAAACTGTGC | TCCAGGAGCT | CCTACAGACA | 1620 |
| CATGCGCAAC | ATGAAGGGGC | TGAGGCAACA | GGCTGTGAGG | GGGCATCGGG | CAGGAGCTTA | 1680 |
| ACCGGAGGGC | CCTGGGGGCC | CCACCCCAAG | CGCTTGGATT | AACCAGGTTC | CGCGGCGGAG | 1740 |
| CTCTCTGCTT | CGTTCTCTGC | TGGAAGAGAC | TCTCTACCCG | GGTGCGGTGG | CTCACGCCTG | 1800 |
| TAATACTAGC | ACGTTGGGGG | GCCGAGGCGG | GCAGATCATG | AGGTTAGGAG | TTCGAGAGCA | 1860 |
| GNCCGACCCA | CATGGTGAAA | CCCCATCTCT | ACTAAAAATA | CAAAAATTAG | CTGGGAGTGG | 1920 |
| TGGTGCGGGG | CCTGTAATCC | CAACTACTCA | GGAGGCTGAG | GCAGGAGAAT | CGCTTGAACT | 1980 |
| CGGGGACGGG | GGGGNGGGCG | GGGAAAGACT | CTCTACAGTG | ACCAGGAGCT | GACCTATCTC | 2040 |

| | | | | | | |
|---|---|---|---|---|---|---|
| CANCAGTGGG | GAGGAGNCCA | TNCAGAAGNC | CTTGGGCATC | CTTAGCCCTC | GCCANCTACG | 2100 |
| AGGGCTGGAA | GAAGGAGAGC | CACCAGGACA | ATGGGGATAA | AGTGATGAGT | AAAGTGGTTC | 2160 |
| CAGATGGGGC | AAGGTGTTCC | GNCTGGAAGT | CGTGGTGGAC | CANCCCATGG | AGAGGCTCTA | 2220 |
| CANAGAGCTC | GTGGAGTGCA | TGGAGGCAAT | GGGGGAGTGC | AACTCCAATA | TCAAGGCGAT | 2280 |
| CAAGGTCTTG | CAGAAGATGA | TCAGAAAAGA | TACATTCATT | GCCCATGAGC | TGGCTGCAGA | 2340 |
| GGCAGCAGGA | AACCTAGTGG | GGCCTTGTGA | CTCTGTGAGC | ATGTGCTGTG | CCAAGCGTCA | 2400 |
| AGGCTCCACC | TGTGTTGCTG | GCTGGCATGG | CCACAGACTT | CGGGAACATG | CCCGAGCAGA | 2460 |
| AGGGTGTCAT | CAGGGGAGC | ATGGTCCCAC | TTGCATGGTG | CTTCACCTGG | TGACTGGAAG | 2520 |
| TCCCTCCAAG | ACCAAACTTA | CATGACTGCT | CAGCATCGAC | CTCAAGGGGT | GGCTTCCCAA | 2580 |
| GAGCATCATC | AACCAGGTCC | TGTCCCAGAC | CCAGGTGGAT | TTTGCCAACC | ACCTGCACAA | 2640 |
| GCGCCTGGAG | TCCCACCCTG | CCTCTGAAGC | CAGGTGTTGA | AGGCCAGCCT | GCTGTTCCCA | 2700 |
| AGTGTGTCCA | GCTGCACTGC | TACACACGCT | TATCAGGAGA | ATCCTTGCTG | GAAGCCTGCA | 2760 |
| AGCTTAAAAT | CTCCATCTGG | CGACAGAGGA | ATAGGTGGGG | TTAGTGTATA | GAGTATGATA | 2820 |
| CTAGGATTCA | GACTGGTAAA | AGTTTTTAGT | ACCAAGAAAA | CAAGGATGAG | GCTCTTTGAT | 2880 |
| TAAAAGGTAA | CTTCATTCAC | TGACTAGCTA | TGACATGAAG | GTTGAGGATC | CTAAAATAAT | 2940 |
| TGTAAAACTT | TTTTTNCTGG | GCCTTTATGT | GNCCACCTAA | AACCATCTTT | AAAATGCTAG | 3000 |
| TGGCTGATAT | GTGTGGGGGG | ATGCTAGTCA | CAGGGCCTGA | GGAGTCTTGC | TTTATGGGCT | 3060 |
| GGAGNACCCC | ATTCCCTGGA | GGCAGAGCAT | GTTCACCAAG | CAGNATCTTA | GAGGGTCTCC | 3120 |
| TNCAGCCCTC | CACTCCNCCA | ANTCGCTNCA | TGGCNACACC | AGATAACAAN | CAGCACCCCN | 3180 |
| CAGTGGGTAC | CTTCCAGAAA | NATAGTCCNA | GCTTTCTCTA | TGGGAAAAGA | CCNANCTAAT | 3240 |
| TAGTAAATAG | GTTTCCCTAT | TGAGTCCATA | GGCACCAGTC | AGAGAAAAGA | ATCATAATTC | 3300 |
| ACACACACAC | ACACACACAC | ACACACACAC | ACACNACCAG | GACCTGAGTT | CAGAAAATGA | 3360 |
| AGCCTGTAAT | CACACACTAA | AATGAAAACA | ATAAATCATG | TGTATTACAG | TTAATAAATG | 3420 |
| AATANNATGT | ATTGCTTCTA | TAGCCTTGTG | ATATGGTTTG | GCTGTGTCTG | CACCCAAATC | 3480 |
| TCATCTT | | | | | | 3487 |

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:5:

GCAGCAGCAG  CGGCAGCAG                                              19

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (synthetic)

(i i i) HYPOTHETICAL: NO (i v) ANTI-SENSE: NO (x i) SEQUENCE DESCRIPTION: SEQ ID NO:6:

ATGAGCGTGT GTACCAGTGC AG                                                                  22

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:7:

GACAAAGTGA TGAGTAAAGT G                                                                   21

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:8:

TGTGGCCATG CCAGCCAGCA                                                                     20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:9:

GTGAGCAAAG TCCAGGTGCG                                                                     20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO ( x i ) SEQUENCE DESCRIPTION: SEQ ID NO:10:

GGATGCAGTC CACATGCTTG G                                                                              21

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:11:

GATACATTCA TTACTCAC                                                                                  18

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:12:

CCTGGCAGCC TGTTTGTGAT AG                                                                             22

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:13:

CCTCATGTCA TAGCTAATCA GTG                                                                            23

( 2 ) INFORMATION FOR SEQ ID NO:14:

( i ) SEQUENCE CHARACTERISTICS:
        ( A ) LENGTH: 183 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TGTCAAGGAG ATCAAGGTGA GCAAAGTCCA GGTGCGGGTG GCAGGGGCCC AGGAGAGCCC                                     60

| AGTGTGAATG | CTGTATCAAA | GAGAGGACCC | CTAGCTGTGG | GGGGTGCTTA | GCCCAACACA | 120 |
| GGCTGAGTCG | TGATTCTGGT | TCCCCATGGC | CTGGTAGGTC | CTGCAGAAGA | TCGGAAAAGA | 180 |
| TAC | | | | | | 183 |

( 2 ) INFORMATION FOR SEQ ID NO:15:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

| AGAAGGGTGT | CATCAGGTAA | TACGGGNAGN | AGGCTCCAAA | CCCCCCTCTT | CTAACACAGG | 60 |
| CCTGCAGGTG | TGCACCCAAG | CATGTGGACT | GCATCCCCAG | CTCCAAGAAA | CCA | 113 |

( 2 ) INFORMATION FOR SEQ ID NO:16:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

| TAAACAACCA | GTTCNAGAGA | GNANTCNCNN | CTTTCCCCCT | NACTTGACTT | GCCCCAATTT | 60 |
| CCAGGGCGGA | GCACGGTCCC | ACTT | | | | 84 |

( 2 ) INFORMATION FOR SEQ ID NO:17:

( i ) SEQUENCE CHARACTERISTICS:
        ( A ) LENGTH: 133 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

| ACTCAGCATC | GACCTCAAGG | TGAAGGGCAT | GGGAGGGGGA | CCTGGAAGGC | AGGTGGTAGT | 60 |
| GAGAAAAACA | GGCTCTTCCC | ATTCCCCCA | TGGTGGAGAA | AGAATCCTCT | TCTATTCTGA | 120 |
| TAGAATCACA | GGC | | | | | 133 |

( 2 ) INFORMATION FOR SEQ ID NO:18:

( i ) SEQUENCE CHARACTERISTICS:
        ( A ) LENGTH: 110 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

CCCTGGCAGC CTGTTTGTGA TAGGGCGCAG TGTCAAGAGT GGGCCAAAAC CCACAAGATG 60

GCCAAATTCT CCTACCTCCT ACTGCAGGGG TGGCTGCCCA AGAGCATCAT 110

( 2 ) INFORMATION FOR SEQ ID NO:19:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:19:

AGCCTCACCG GCGTTGGCGG 20

( 2 ) INFORMATION FOR SEQ ID NO:20:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:20:

CTGCAAGACC TTGATCGCCT TG 22

( 2 ) INFORMATION FOR SEQ ID NO:21:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:21:

AGAAAGCGCT GCAGGAATAC C 21

( 2 ) INFORMATION FOR SEQ ID NO:22:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:22:

GTGACGTGCA GAGCTCTC 18

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:23:

GAAACTGGGC GAATCTAC 18

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:24:

TTGAAACACC CCAAACACTG 20

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:25:

AAAAGAACGC TGTGTGGCTG GGAC 24

( 2 ) INFORMATION FOR SEQ ID NO:26:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:26:

ACCTAAACCG TGGCAAAT                                                                                                18

( 2 ) INFORMATION FOR SEQ ID NO:27:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:27:

CCTACTGGAA GCCTGCAAGT CTAAG                                                                                         25

( 2 ) INFORMATION FOR SEQ ID NO:28:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:28:

TGGTTTTAGG TGGGTACATA AGGG                                                                                          24

( 2 ) INFORMATION FOR SEQ ID NO:29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:29:

AAGCGCCGAG GCTCC                                                                                                    15

( 2 ) INFORMATION FOR SEQ ID NO:30:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:30:

ATCAACCAGG TC                                                                                                       12